(12) United States Patent
Neuman et al.

(10) Patent No.: US 6,372,721 B1
(45) Date of Patent: *Apr. 16, 2002

(54) METHOD FOR INDUCING DNA SYNTHESIS IN NEURONS

(75) Inventors: Toomas Neuman, Fort Collins, CO (US); Kikuo Suda, Shizuoka (JP); Howard O. Nornes, Fort Collins, CO (US)

(73) Assignee: Spinal Cord society, Fergus Falls, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/408,508

(22) Filed: Sep. 30, 1999

Related U.S. Application Data

(63) Continuation of application No. 08/362,495, filed as application No. PCT/US94/14614 on Dec. 19, 1994, now Pat. No. 6,087,171, which is a continuation-in-part of application No. 08/301,416, filed on Sep. 8, 1994, now abandoned, which is a continuation-in-part of application No. 08/169,522, filed on Dec. 17, 1993, now abandoned.

(51) Int. Cl.$^7$ .................. A61K 31/7088; A61K 31/711; C12N 15/87; C12N 15/88
(52) U.S. Cl. ................... 514/44; 435/69.1; 435/375; 435/455; 435/458; 435/465
(58) Field of Search ............................. 435/320.1, 375, 435/455, 458, 465, 466, 69.1; 514/44; 424/450; 536/23.1, 23.72, 24.1

(56) References Cited

U.S. PATENT DOCUMENTS

| | | | | |
|---|---|---|---|---|
| 5,473,056 A | * | 12/1995 | Ivey-Hoyle et al. | 530/358 |
| 5,631,158 A | * | 5/1997 | Dorai et al. | 435/464 |
| 5,759,803 A | * | 6/1998 | Kaelin, Jr. et al. | 435/69.1 |
| 6,087,171 A | * | 7/2000 | Neuman et al. | 435/375 |

FOREIGN PATENT DOCUMENTS

| | | | |
|---|---|---|---|
| WO | 99/09057 | * | 2/1999 |

OTHER PUBLICATIONS

Ghadge et al. CNS delivery by retrograde transport of recombinant replication–defective adenoviruses. Gene Therapy (1995) 2: 132–137.*

Sahenk et al. Gene delivery to spinal motor neurons. Brain Research (1993) 606: 126–129.*

Ugolini, G. Transneuronal transfer of herpes simplex virus type 1 (HSV!) from mixed limb nerves to the CNS. I. Sequence of transfer from sensory, motor, and sympathetic nerve fibers to the spinal cord. J. Comp. Neurology 1992) 326: 527–548.*

Crystal, R. G. Transfer of genes to humans: Early lessons and obstacles to success. Science 270: 404–410, 1995.

Report and recommendations of the panel to assess the NIH investment in research on gene therapy, Orkin and Motulsky, co–chairs. National Institutes of Health, Dec. 1995.

Suda et al., "DNA synthesis is induced in adult neurons after expression of E2F1 and E1A," NeuroReport, 5:1749–51 (1994).

Terry, "Regeneration in Alzheimer Disease and Aging," Advances in Neurology, 59:1–4 (1993).

Koliatsos et al., "Evidence That Brain–Derived Neurotrophic Factor Is a Trophic Factor for Motor Neurons In Vivo," Neuron, 10:359–367 (1993).

Hunter, "Braking the Cycle," Cell, 75:839–841 (1993).

Johnson et al., "Expression of transcription factor E2F1 induces quiescent cells to enter S phase," Nature, 365:349–352 (1993).

Zhu et al., "Inhibition of cell proliferation by p107, a relative of the retinoblastoma protein," Genes & Development, 7:1111–25 (1993).

Okano et al., "RB and Cdc2 Expression in Brain: Correlations with .sup.3 H–Thymidine Incorporation and Neurogenesis," The Journal of Neuroscience, 13:2930–38 (1993).

Gu et al., "Interaction of Myogenic Factors and the Retinoblastoma Protein Mediates Muscle Cell Commitment and Differentiation," Cell, 72:309–324 (1993).

Schwarz et al., "Interactions of the p107 and Rb proteins with E2F during the cell proliferation response," The EMBO Journal, 12:1013–20 (1993).

Yan et al., "Brain–derived neurotrophic factor rescues spinal motor neurons from axotomy–induced cell death," Nature, 360:753–755 (1992).

(List continued on next page.)

Primary Examiner—John L. LeGuyader
Assistant Examiner—Thomas G Larson
(74) Attorney, Agent, or Firm—Patterson, thuente, Skaar & Christensen, P.A.

(57) ABSTRACT

A method is provided for inducing DNA synthesis in differentiated neurons. According to certain embodiments of the invention, a method for inducing DNA synthesis in a differentiated neuron is provided that includes obtaining a vector comprising nucleic acid encoding an E2F regulator and/or an E1A regulator, wherein the vector can be used to express the nucleic acid in a differentiated neuron, and transfecting a differentiated neuron with the vector. According to certain embodiments of the invention, a method for integrating DNA encoding a desired protein in a differentiated neuron is provided that includes obtaining a vector comprising nucleic acid encoding an E2F regulator and/or an E1A regulator, wherein the vector can be used to express the nucleic acid in a neuron, obtaining DNA encoding a desired protein, and cotransfecting a differentiated neuron with the vector and the DNA encoding the desired protein such that the DNA encoding the desired protein is integrated in the differentiated neuron and the desired protein is produced.

26 Claims, 3 Drawing Sheets

OTHER PUBLICATIONS

Devoto et al., "A Cyclin A–Protein Kinase Complex Possesses Sequence–Specific DNA Binding Activity: p33.sup.cdk2 Is a Component of the E2F–Cyclin A Complex," Cell, 68:167–176 (1992).

Zambetti et al., "Wild–type p53 mediates positive regulation of gene expression through a specific DNA sequence element," Genes & Development, 6:1143–52 (1992).

Pagano et al., "Association of cdk2 Kinase with the Transcription Factor E2F During S Phase," Science, 255:1144–47 (1992).

Kaelin, Jr., et al., "Expression Cloning of a cDNA Encoding a Retinoblastoma–Binding Protein with E2F–like Properties," Cell, 70:351–364 (1992).

Lee et al., "Mice deficient for Rb are nonviable and show defects in neurogenesis and haematopoiesis," Nature, 359:288–294 (1992).

Jacks et al., "Effects of an Rb mutation in the mouse," Nature, 359:295–300 (1992).

RayChaudhuri et al., Escherichia coli cell–division gene ftsZ encodes a novel GTP–binding protein, Nature, 359:251–254 (1992).

Dalton, "Cell cycle regulation of the human cdc2 gene," The EMBO Journal, 11:1797–1804 (1992).

Shirodkar et al., "The Transcription Factor E2F Interacts with the Retinoblastoma Product and a p107–Cyclin A Complex in a Cell Cycle–Regulated Manner," Cell, 68:157–166 (1992).

Helin et al., "a cDNA Encoding a pRB–Binding Protein with Properties of the Transcription Factor E2F," Cell, 70:337–350 (1992).

Chellappan et al., "Adenovirus E1A, simina virus 40 tumor antigen, and human papillomavirus E7 protein share the capacity to disrupt the interaction between transcription factor E2F and the retinoblastoma gene products," Proc. Natl. Acad. Sci. USA, 89:4549–53 (1992).

Cao et al., "Independent binding of the retinoblastoma protein and p107 to the transcription factor E2F," Nature, 355:176–179 (1992).

Neuman et al., "ME1 and GE1: Basic Helix–Loop–Helix Transcription Factors Expressed at High Levels in the Developing Nervous System and in Morphogenetically Active Regions," European Journal of Neuroscience, 5:311–318 (1992).

Oin et al., "Identification of a growth suppression domain within the retinoblastoma gene products," Genes & Development, 6:953–964 (1992).

Takahashi et al., "BUdR as an S–phase marker for quantitative studies of cytokinetic behaviour in the murine cerebral ventricular zone," Journal of Neurocytology, 21:185–197 (1992).

Nevins, "E2F: A Link Between the Rb Tumor Suppressor Protein and Viral Oncoproteins," Science, 258:424–429 (1992).

Hiebert et al., "The interaction of RB with E2F coincides with an inhibition of the transcriptional activity of E2F," Genes & Development, 6:177–185 (1992).

Zamanian et al., "Adenovirus Ela prevents the retinoblastoma gene product from repressing the activity of a cellular transcription factor," EMBO Journal, 11:2603–10 (1992).

Wientraub et al., "Retinoblastoma protein switches the E2F site from positive to negative element," Nature, 358:259–262 (1992).

Hamel et al., "Transcriptional Repression of the E2–Containing Promoters EIIaE c–myc, and RB1 by the Product of the RB1 Gene," Molecular and Cellular Biology, 12:3431–38 (1992).

Tuszynski et al., "Recombinant Human Nerve Growth Factor Infusions Prevent Cholinergic Neuronal Degeneration in the Adult Primate Brain," Annals of Neurology, 30:625–636 (1991).

Phillips et al., "BDNF mRNA Is Decreased in the Hippocampus of Individuals with Alzheimer's Disease," Neuron, 7:695–702 (1991).

MacGregor et al., "Use of E. coli lacZ (.beta.–Galactosidase) as a Reporter Gene," Methods in Molecular Biology, 7:217–235 (1991).

Goodrich et al., "The Retinoblastoma Gene Product Regulates Progression through the G1 Phase of the Cell Cycle," Cell, 67:293–302 (1991).

Mudryj et al., "Cell Cycle Regulation of the E2F Transcription Factor Involves an Interaction with Cyclin A," Cell, 65:1243–53 (1991).

Chellappan et al., "The E2F Transcription Factor Is a Cellular Target for the RB Protein," Cell, 65:1053–61 (1991).

Alderson et al., "Brain–Derived Neurotrophic Factor Increases Survival and Differentiated Functions of Rat Septal Cholinergic Neurons in Culture," Neuron, 5:297–306 (1990).

Altman et al., "Migration and Distribution of Two Populations of Hippocampal Granule Cell Precursors During the Perinatal and Postnatal Periods," The Journal of Comparative Neurology, 301:365–381 (1990).

Holmberg et al., "Highly Efficient Immunoliposomes Prepared with a Method Which is Compatible with Various Lipid Compositions," Biochemical and Biophysical Research Communications, 165:1272–78 (1989).

Bernards et al., "Structure and expression of the murine retinoblastoma gene and characterization of its encoded protein," Proc. Natl. Acad. Sci. USA, 86:6474–78 (1989).

Goetz et al., "Multicenter Study of Autologous Adrenal Medullary Transplantation to the Corpus Striatum in Patients with Advanced Parkinson's Disease," The New England Journal of Medicine, 320:337–341 (1989).

Hofer et al., "Brain–derived neurotrophic factor prevents neuronal death in vivo," Nature, 331:261–262 (1988).

Hansen et al., "Adrenal Medullary Autografts into the Basal Ganglia of Cebus Monkeys: Graft Viability and Fine Structure," Experimental Neurology, 102:65–75 (1988).

D'Mello et al., "Isolation and Nucleotide Sequence of a cDNA Clone Encoding Bovine Adrenal Tyrosine Hydroxylase: Comparative Analysis of Tyrosine Hydroxylase Gene Products," Journal of Neuroscience Research, 19:440–449 (1988).

Levi–Montalcini, "The Nerve Growth Factor 35 Years Later," Science, 237:1154–62 (1987).

Freed et al., "Intrastriatal adrenal medulla grafts in rats," J. Neurosurg. 65:664–670 (1986).

Lindvall et al., "Transplantation in Parkinson's Disease: Two Cases of Adrenal Medullary Grafts to the Putamen," Annals of Neurology, 22:457–468 (1986).

Bayer, "Changes in the Total Number of Dentate Granule Cells in Juvenile and Adult Rats: A Correlated Volumetric and .sup.3 H–Thymidine Autoradiographic Study," Exp. Brain Res., 46:315–323 (1982).

Pfeiffer et al., "Differentiation of a Teratocarcinoma Line: Preferential Development of Cholinergic Neurons," The Journal of Cell Biology, 88:57–66 (1981).

Kaplan et al., "Neurogenesis in the Adult Rat: Electron Microscopic Analysis of Light Radioautographs," Science, 197:1092–94 (1977).

Angevine et al., "Autoradiographic Study of Cell Migration during Histogenesis of Cerebral Cortex in the Mouse," Nature, 192:766–768 (1961).

* cited by examiner

E1A  NF  BrdU

METHOD FOR INDUCING DNA SYNTHESIS IN NEURONS

This is a continuation of U.S. patent application Ser. No. 08/362,495, filed Nov. 18, 1996, now U.S. Pat. No. 6,087, 171, which is the National Stage of International Application No. PCT/US94/14614, filed Dec. 19, 1994, which is a continuation-in-part of U.S. patent application Ser. No. 08/301,416, filed Sep. 8, 1994, now abandoned, which is a continuation-in-part of U.S. patent application Ser. No. 08/169,522, filed Dec. 17, 1993, now abandoned, each of which is being relied upon and is incorporated herein by reference.

In the parent application Serial No. 08/169,522, the term E2F is used to describe a regulator involved in cell cycle regulation. The present inventors are presently aware of at least three types of E2F regulators (E2F1, E2F2, and E2F3). The inventors now know that the E2F regulator used in the examples of the parent application Ser. No. 08/169,522 was E2F1. In this continuation-in-part application and in the parent application Ser. No. 08/301,416, use of the term "E2F" (without a number after the "F") is generic to all forms of E2F.

In the parent application Ser. No. 08/169,522, a protein $p105^{Rb}$ is discussed. In the present application and in the parent application Ser. No. 08/301,416, the term Rb is used to represent the same protein.

BACKGROUND AND SUMMARY OF THE INVENTION

The mammalian nervous system has no mechanisms to replace lost neurons with the exception of some regions where neurogenesis continues throughout life (Kaplan et al., *Science*, 197:1092–1094 (1977); Bayer, *Exp. Brain Res.*, 46: 315–3323 (1982); Altman et al., *J. Comp. Neurol.*, 301:365–381 (1990)). Neurons are born during a narrow window of time and, when differentiated, become blocked at the early G1(G0) phase of the cell cycle (Angevine et al., *Nature*, 192:766–768 (1961); Takahashi et al., *J. Neurocytol.*, 21:185–197 (1992)). Accordingly, differentiated neurons are not capable of proceeding from the G1(G0) phase to the DNA synthesis phase. Thus, differentiated neurons are not only incapable of synthesizing DNA, but also are incapable of proceeding through the rest of the cell cycle to form new cells (proliferating).

It would be advantageous if one could cause normally differentiated neurons to proceed from the G1(G0) phase to the DNA synthesis phase. By doing so, one could induce proliferation of such neurons to produce new cells.

Moreover, as demonstrated by the present inventors, one can use gene therapy by stably integrating DNA into normally differentiated neurons that have been induced to proceed from the G1(G0) phase to the DNA synthesis phase. Gene therapy involves incorporating nucleic acid into the patient host. In certain applications, the host will express the foreign nucleic acid such that a therapeutic protein is made in the host. Although gene therapy has been used to express nucleic acids in nondifferentiated cells that can proliferate and synthesize nucleic acid, unique issues exist for gene therapy involving transfer of nucleic acid into neurons.

For gene therapy, one should consider factors involved in the delivery of the nucleic acid into the target cell and efficient expression of the nucleic acid in the cell. For therapy involving neurons as the target cells, customarily, one would transfer the nucleic acid in vivo to postmitotic (nonproliferating and fully differentiated) cells. Therapy for diseases of or trauma to the central nervous system may involve use of differentiated neurons as the target cells.

Physical and viral vector methods have been used for gene transfer into neurons of the adult nervous system with limited success. Direct injection of DNA into neurons is possible, however, this is limiting because of the number of cells involved.

Although liposomes, complex ligand DNA conjugates, or viral vectors can deliver DNA to differentiated cells, the subsequent expression of DNA is transient since such cells do not normally synthesize DNA. Gene therapy would be somewhat limited if only transient expression of the transferred DNA was achieved rather than stable functional integration of the transferred DNA because of the shorter periods of expression associated with transient expression.

For many conditions, one desires expression of the DNA over an extended period of time to provide the therapeutic molecule for ongoing treatment. For example, a patient having Parkinson's disease or Alzheimers disease often needs treatment for many years. Functional integration of transferred DNA would provide such long term expression of the therapeutic molecule. Thus, it would be desirable to have stable functional integration of the transferred DNA into neurons for treatment of neurodegenerative diseases and trauma.

The regulation of G1(G0) to DNA synthesis transition involves regulator molecules known as transcription factors. Modification (mainly phosphorylation) of preexisting regulators and transcriptional activation of new genes occurs during this process. Several different protein kinases which form complexes and modify transcription factors are described (Devoto et al., *Cell*, 68:167–176 (1992), Hunter, *Cell*, 75:839–841 (1993)). Several transcription factors are described which regulate different steps in G1 to DNA synthesis transition. Retinoblastoma antigen (Rb) (Hamel et al., *Molec. Cell. Biol.*, 12:3431–3438 (1992)), sequence specific transcription factor E2F (Nevins, *Science*, 258:424–429 (1992), and tumor suppressor p53 (Zambetti et al., *Genes and Development*, 6:1143–1152 (1992)) play central roles in the initiation of DNA synthesis and the DNA synthesis phase.

Transcription factor E2F is a key molecule in the G1 to DNA synthesis phase transition. E2F regulates expression of genes necessary for DNA synthesis phase initiation and progression. Nevins, *Science*, 258:424–429 (1992); Mudryj et al, *Cell*, 65:1243–1253 (1991); Schwarz et al., *EMBO J.*, 12:1013–1020 (1993). During the early G1 phase, the cellular E2F is in a complex with Rb (Nevins, 1992). In this complex, the E2F is inactive. Also, the Rb/E2F complex is an active repressor of transcription of several S phase genes (Weintraub et al., *Nature*, 358:259–261 (1992)).

Phosphorylation of Rb by cdc2 or cdk kinases releases E2F, which activates the genes necessary in the DNA synthesis phase. Also, adenovirus oncoprotein E1A is a transcriptional regulator that binds Rb, which causes the release of active E2F from the inactive complex with Rb.

During the DNA synthesis phase, the E2F will become inactivated again by forming a complex with cyclin A, cdc2 kinase and p107 (Pagano et al., *Science*, 255:1144–1147 (1992)). Adenovirus oncoprotein E1A also binds p107, which causes release of active E2F from the inactive complexes with p107. Complexes of E1A with Rb and p107 are more stable than E2F complexes with these same proteins; thus, the presence of E1A causes dissociation of E2F complexes with Rb and p107 and the release of transcriptionally active E2F (Nevins, *Science*, 258:424–429 (1992)).

Different forms of E2F exist in different cell types (Kaelin et al., *Cell*, 70:351–364 (1992). The homology between cell cycle regulatory factors from different species (e.g., from yeast to humans), however, is very high. Accordingly, one can accurately predict the action of such factors in the cell cycle regulation from one species to another.

Although the present inventors do not intend to be limited to any theory of why differentiated neurons do not synthesize DNA, since mature neurons in cerebral cortex and cerebellum express Rb (Okano et al., *J. Neurosci.*, 13:2930–2938 (1993) and Bernards et al., *Proc. Nat. Acad. Sci. U.S.A.*, 86:6474–6478 (1989)) and E2F (Helin et al, *Cell*, 70:337–350 (1992)) at relatively high levels, one hypothesis of the inventors is that the cell cycle is blocked by formation of inactive complexes between Rb and E2F in these neurons. Alternatively, Rb may have an important role in differentiation and functioning of neurons.

An object of the present invention is to provide methods of inducing DNA synthesis in normally differentiated cells such as neurons. Another object according to certain embodiments of the present invention is to induce normally differentiated cells such as neurons to proliferate.

The present inventors have shown that transfecting neurons with DNA encoding transcription factor E2F1 and viral oncoprotein E1A in vitro and in vivo results in the induction of DNA synthesis in these neurons. The present inventors have also shown that such transfection in vivo, followed by induction of DNA synthesis, can be applied to stably integrate a functional gene(s) that is also transfected into the neuron.

By inducing differentiated neurons to synthesize DNA, the present invention provides for production of protein in neurons. With stable and functional integration, the present invention also provides for gene therapy in which normally differentiated neurons are induced to produce a given therapeutic protein. Also, by commencing the cell cycle from the G1(G0) phase to DNA synthesis, the present invention is also directed to inducing proliferation of neurons to produce new cells.

Another object of the present invention is to provide a method for isolating DNA that encodes molecules that regulate or induce DNA synthesis or proliferation of differentiated cells such as neurons. The method includes (a) preparing a subtraction cDNA library, (b) cloning individual cDNAs into individual vectors to create an expression library, transfecting differentiated cells with the expression library, (c) selecting transfected cells that synthesize DNA or proliferate, (d) isolating cDNAs from the selected cells, and (e) selecting cDNAs other than cDNAs known to encode molecules that regulate or induce cells progressing to the DNA synthesis phase of the cell cycle.

The method according to certain embodiments further includes the step of amplifying isolated cDNAs from steps (d) and (e) in a polymerase chain reaction. The amplified cDNAs may then be cloned into an expression vector which is transfected into differentiated cells such as neurons to induce DNA synthesis and/or proliferation.

DNA isolated when using such methods are also provided.

Another object according to certain embodiments of the invention is to use DNA encoding molecules that induce differentiated cells to synthesize DNA to isolate homologous genes from other organisms including humans, to produce proteins and antibodies against proteins for which these genes code, and to induce differentiated cells such as neurons to proliferate. The antibodies can be used for diagnostic purposes or for treatment of conditions such as cancer where the patient already produces too much of the molecule that induces DNA synthesis.

Another object according to certain embodiments of the present invention is that it enables one to use neurons from the same individual to obtain (induce the production of) more neurons. Thus, it is possible to replace lost neurons after injury or neurodegenerative diseases.

Another object according to certain embodiments of the present invention is to induce differentiated cells such as neurons to produce proteins in vitro or in vivo by inducing DNA synthesis in such differentiated cells.

Other objects and advantages will become apparent upon review of this patent application.

BRIEF DESCRIPTION OF THE FIGURES

FIG. 2. Induction of DNA synthesis in cortical neurons in vivo.

DETAILED DESCRIPTION OF PREFERRED EMBODIMENTS

Figure 1:
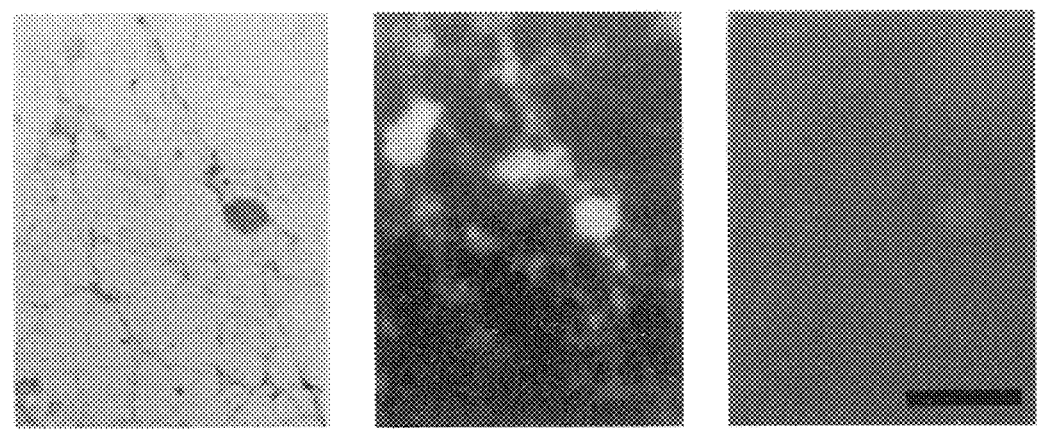
FIG. 1. Induction of DNA synthesis in differentiated cerebellar neurons in vitro. Differentiated cerebellar granular neurons were transfected with $E1A^{13S}$ cDNA and immunostained for E1A expression (left panel), NF-H expression (middle panel), and BrdU incorporation (right panel).

The present invention is directed to inducing DNA synthesis in neurons, which in certain embodiments provides for production of proteins, peptides, or polypeptides (for simplicity, the term "protein" is used to encompass all of these materials) in neurons, for gene therapy that produces proteins in normally differentiated neurons, and for inducing proliferation of neurons to produce new cells. According to the present invention, stable integration of delivered genes into the genome of neurons is accomplished. According to certain embodiments of the present invention, the method includes transfection of postmitotic neurons with DNA which induces DNA synthesis along with additional DNA that has potential therapeutic effect, such as DNA that encodes a therapeutic protein. In certain embodiments, the DNA is mixed, packaged into liposomes, and injected into the central nervous system.

The present inventors have demonstrated that DNA synthesis occurred in adult neurons and that expression of introduced DNA was stable for months. With stable integration of the delivered gene into the genome of the target neurons, this method of gene transfer provides for gene therapy for neurodegenerative diseases such as Parkinson's, Huntington's and Alzheimer's and for reconstruction following trauma and stroke. Further, this method can be used for gene transfer to any nonproliferating and fully differentiated cell of the body, since regulation of the cell cycle is not unique to neurons, and induction of DNA synthesis should result in stable integration of cotransfected DNA.

According to certain embodiments, the invention involves transfection and expression of cell cycle regulatory factors in the differentiated target cells to induce DNA synthesis. Examples of transcriptional regulators according to certain embodiments include E1A and E2F. In view of the interaction of Rb and E2F, however, other factors that bind to Rb and thus free E2F from RB/E2F complexes can also be used according to certain embodiments. The present invention should not be limited to any particular regulatory factors, however, since the inventors have shown for the first time that differentiated cells such as neurons can be induced to synthesize DNA (by proceeding to the DNA synthesis phase of the cell cycle). with that knowledge, one skilled in the art would be able to carry out the present invention with other regulators in the cell cycle.

Foreign DNA encoding therapeutically relevant proteins can be introduced into neurons before or during the induced DNA synthesis phase, which accomplishes a stable and functional integration of the foreign DNA into neurons of a different organism including a human. In certain embodiments, the foreign DNA is cotransfected with DNA encoding the transcription or regulatory factor. This provides gene-based therapies of the central nervous system (CNS).

In the case of Parkinson's disease, cDNA encoding tyrosine hydroxylase, which is a key enzyme in the synthesis of L-DOPA and dopamine, can be introduced into catecholamine producing neurons; for other neurodegenerative diseases and for stroke and trauma patients, genes expressing neurotrophic factors can be introduced to promote regeneration. In conditions which require cell replacement, neurons can be induced to proceed through the cell cycle and form new cells.

According to certain embodiments of the invention, a method for inducing DNA synthesis in a differentiated neuron is provided that includes obtaining a vector comprising nucleic acid encoding an E2F regulator and/or an E1A regulator, wherein the vector can be used to express the nucleic acid in a differentiated neuron, and transfecting a differentiated neuron with the vector.

According to certain embodiments of the invention, a method for integrating DNA encoding a desired protein in a differentiated neuron is provided that includes obtaining a vector comprising nucleic acid encoding an E2F regulator and/or an E1A regulator, wherein the vector can be used to express the nucleic acid in a neuron, obtaining DNA encoding a desired protein, and cotransfecting a differentiated neuron with the vector and the DNA encoding the desired protein such that the DNA encoding the desired protein is integrated in the differentiated neuron and the desired protein is produced.

The following examples illustrate aspects of the invention. These examples are for illustrative purposes only and are not intended to limit the scope of the invention.

EXAMPLE 1

Efficiency Of Initiation Of DNA Synthesis Followed By Proliferation Of Neuronally Differentiated PCC7 Cells After Transfection Of E1A And E2F cDNAs The ability of E2F and E1A to induce DNA synthesis in postmitotic neurons was first tested in mouse teratocarcinoma cell line PCC7.

Mouse teratocarcinoma cell line PCC7 was grown in Dulbecco's modified Eagle medium containing 10% fetal calf serum (Sigma). Neuronal differentiation of PCC7 cells was induced with dibutyryl cyclic AMP ($Bt_2cAMP$, 1 mM) and all-trans retinoic acid (RA, 0.5 $\mu$M).

Mouse E2F1 (mE2F1), RNP-1 and RNP-2 were cloned into pRcCMvneo expression vector (obtained from Invitrogen Corporation) between HindIII and NotI sites. Adenovirus E1A 12S and 13S cDNAs (obtained from Dr. J. Nevins and Dr. E. Moran) and mouse ME1 were cloned into pRcCMV vector using HindIII linkers.

PCC7 cells were differentiated 3 days before transfection. Transfection of the cDNAs was performed by the calcium phosphate coprecipitation technique using 20 $\mu$g of DNA per 100 mm tissue culture plates (Falcon) at a cell density of $2\times10^6$ cells per plate with an incubation time of 15–16 h. The transfectant cells which were stably proliferating were identified following culture of cells in the presence of 400 $\mu$g/ml G418 (Gibco) for 18–21 days and the number of proliferating clones was counted.

The cDNA was isolated from the proliferating clones, and the efficiency of isolated cDNAs to dedifferentiate and initiate proliferation of neuronally differentiated PCC7 cells was tested in two conditions: (1) transfection of cDNAs into neuronally differentiated PCC7 cells (same conditions used in screening the expression library), (2) transfection of cDNAs into proliferating PCC7 cells followed immediately by treatment with RA and $Bt_2cAMP$ to induce neuronal differentiation.

The cDNAs mE2F and adenovirus oncogenes E1A 12S and 13S forms induced the formation of proliferating clones (Table 1). Helix-loop-helix transcription factor ME1 was used as a control cDNA. ME1 is expressed in many proliferating cell types, and its expression is down-regulated during differentiation (Neuman et al., *European J. Neurosci.*, 5:311–318 (1993)). In neuronally differentiated PCC7 cells, both 12S and 13S forms of E1A block differentiation and initiate proliferation (Table 1) at 70–100 times higher efficiency than mE2F1. No proliferating clones were observed in ME1 transfected culture dishes.

TABLE 1

| | Number of Clones | |
|---|---|---|
| Construct | Transfection into un-differentiated cells followed by differentiation | Transfection into differentiated cells |
| pRcCMV | 0/0/0 | 0/0/0 |
| pRcCMV-E1A12S | 150/231/112 | 146/219/110 |
| pRcCMV-E1A13S | 184/191/132 | 172/180/109 |
| pRcCMV-E2F | 25/19/14 | 15/19/12 |
| pRcCMV-RNP-1 | 9/11/15 | 12/12/15 |
| pRcCMV-RNP-2 | 12/9/17 | 9/11/16 |
| pRcCMV-ME1 | 0/0/0 | 0/0/0 |

Results of three separate experiments are presented. All transfections were performed in triplicates and each number represents the average number of clones from three culture dishes. The results are normalized to the transfection efficiency measured by beta-galactosidase activity after cotransfection of lacZ driven by CMV promoter.

Figure 3:
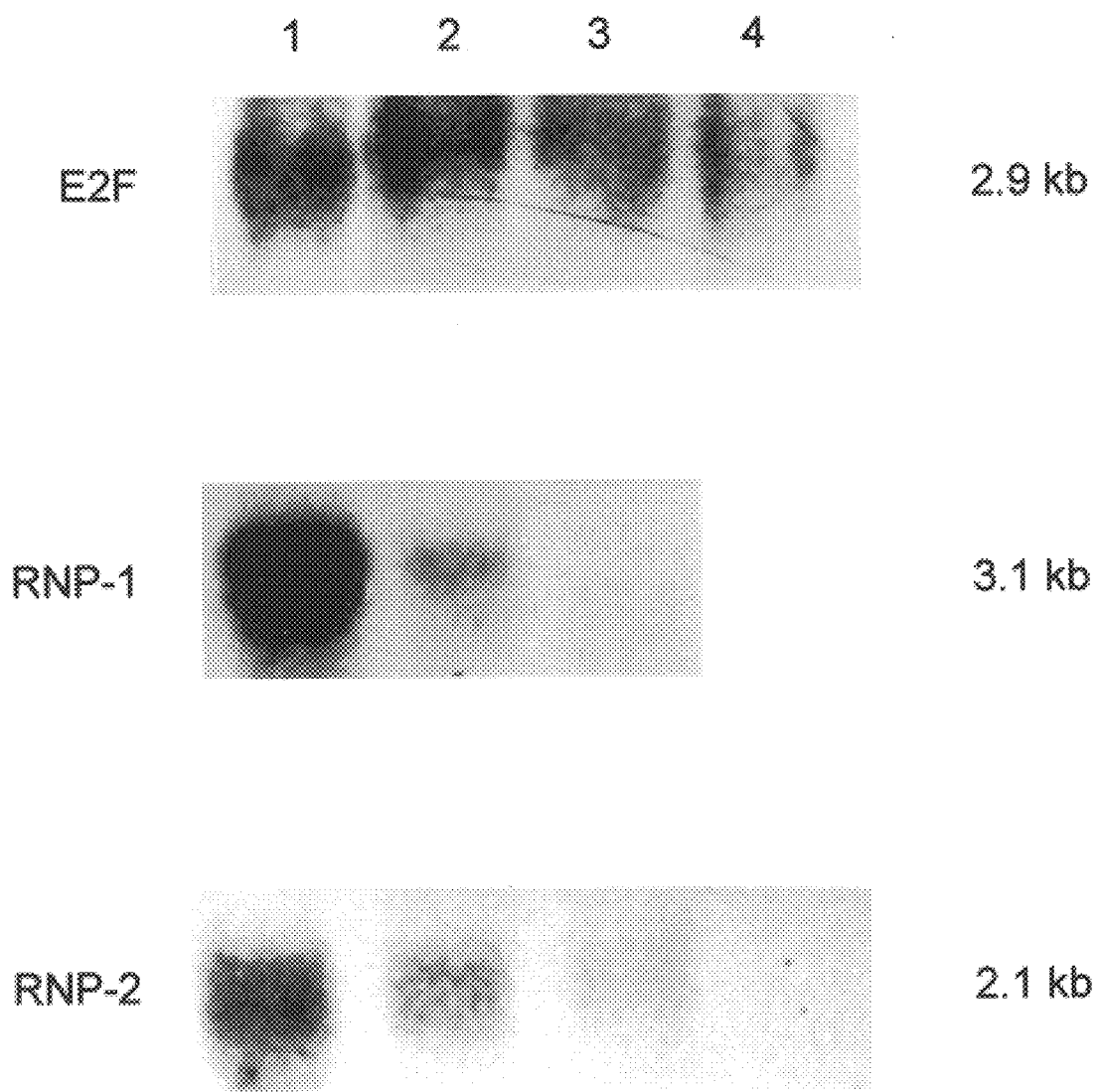
FIG. 3 shows the Northern blot analysis of EZF, RNP-1 and RNP-2 expression during differentiation of teratocarcinoma PCC7 cells.

Northern blot analyses was performed to characterize the expression of E2A, RNP-1 and RNP-2 genes in differentiating PCC7 cells. The RNA was fractionated on 1.2% agarose formaldehyde gel and transferred to a nylon membrane (Hybond N, Amersham). Twenty-five micrograms of total RNA were run in each lane. RNA was isolated using acid guanidinium/phenol/chloroform extraction procedure (Chomszynski and Sacchi, 1987. Single-Step Method of RNA Isolation by Acid Guanidinium Thiocyanate-phenol-chloroform Extraction. Analyt. Biochem., 162, 156–159.). The full-length radiolabeled (32P) mE2F, RNP-1 and RNP-2 cDNAs were used as probes. The blots were washed at high stringency (0,2×SSC, 65° C.) and exposed to X-ray film for three days. The amount and quality of transferred RNA were monitored by methylene blue staining of the filters before hybridization. Only the filters with equal amounts of RNA in each lane were used for hybridization. All three genes, E2F, RNP-1 and RNP-2, are down-regulated during neuronal differentiation of PCC7 cells. Down-regulation of E2F is not significant (FIG. 3) which is not surprising as it is expressed in the adult nervous system (Helin et al., 1992. A cDNA Encoding a pRB-Binding Protein with Properties of the Transcription Factor E2F. Cell, 70, 337–350). RNP-1 is down-regulated significantly during the first 24 hours of differentiation, and its mRNA is undetectable by 48 hours. Down-regulation of RNP-2 occurs more gradually, and its mRNA disappears by the third day of differentiation (FIG. 3). The expression pattern of RNF-1 and RNP-2 clearly demonstrates that these genes are expressed in proliferating cells and are downregulated during neuronal differentiation which supports the idea that there are regulators of proliferation and can be used as inducers of proliferation of neurons.

FIG. 3 shows the Northern blot analyses of E2F, RNP-1 and RNP-2 expression during differentiation of teratocarcinoma PCC7 cells. RNA was isolated from untreated (line 1) and 1, 2 and 3 days differentiated cells (respectively lines 2, 3, and 4).

EXAMPLE 2
Induction Of DNA Synthesis In Differentiated Granular Neurons From Mouse Cerebellum Using Mouse E2F And Adenovirus E1A cDNAs A procedure similar to the procedure described in Example 1 to induce DNA synthesis in postmitotic neurons was tested using mouse cerebellar granular neurons. Cerebella of 6 day old mice were dissociated into single cells after incubation in 0.25% trypsin, 1 mM EDTA for 15 minutes at 37° C. Trypsin digestion was stopped by DMEM plus 10% fetal calf serum containing 0.1% DNase. Cells ($3-4 \times 10^5$/ml) were cultured on poly-L-lysine (5 μg/cm$^2$) and collagen (100 μg/ml) coated 4 chamber culture slides (Lab-Tek) in BME medium containing 10% fetal calf serum, 25 mM KCl, and basic fibroblast growth factor (b-FGF) (50 ng/ml). Cytidine arabinoside (10 μM) was present in culture media during days 2–4 to block proliferation of non-neuronal cells.

After 6 days in culture, the cells were transfected by the Transfectam transfection procedure using 5 μg of the pRcCMVneo eukaryotic expression vector (Invitrogen), ME1 cDNA cloned into pRcCMVneo (pRcCMV-ME1), ME2 cDNA cloned into pRcCMVneo (pRcCMV-ME2), E1A$^{13S}$ cDNA cloned into pRcCMVneo (pRcCMV-E1A$^{13S}$), or E2F1 cDNA cloned into pRcCMVneo (pRcCMV-E2F1). The cells were exposed to the DNA for 3–5 hours in DMEM (Gibco) serum free media and then placed in growth media containing insulin-like growth factor 1 (IGF-1) (20 ng/ml). BrdU (final concentration of 10 μM) was added and the cells were incubated for another 24 hours before fixation with cold methanol.

For triple staining, cells were initially incubated with E1A mouse monoclonal antibody (Oncogene Science, 10 μg/ml in 0.01% BSA/PBS) or E2F mouse monoclonal antibody (Santa Cruz, 10 μg/ml in 0.01% BSA/PBS) overnight at 4° C. E1A and E2F were visualized using Vectastain ABC kit (Vector Laboratories) and 3,3'-diaminobenzidine tetrahydrochloride as a substrate for horseradish peroxidase.

After washing three times, the cells were incubated with rabbit anti-neurofilament-200 polyclonal antibody (Sigma, 1:80 in 0.01% BSA/PBS) to detect neurofilament heavy subunit (NF-H), followed by FITC-conjugated goat anti-rabbit IgG (Sigma, 1:100 in 0.01 % BSA/PBS). After washing, the cells were treated with 2M HCl for 30 minutes at room temperature, neutralized with borate buffer (pH 8.5), and immunostained with a rat monoclonal anti-BrdU antibody (Accurate SeraLab, 1:10 in 0.01% BSA/PBS) followed by TRITC-conjugated rabbit anti-rat IgG (Sigma, 1:20 in 0.01% BSA/PBS). The presence of 3,3-diaminobenzidine precipitate and FITC and TRITC fluorescence were then examined using fluorescence microscopy with the appropriate filters to observe triple stained cells.

Cerebellar granular cells isolated from postnatal day 6 mice differentiate and maintain a differentiated state in vitro. After 6 days in culture, no DNA synthesis was detected in granular neurons based on 5-bromo-2'-deoxyuridine (BrdU) incorporation and on immunostaining for neurofilament heavy subunit (NF-H) to identify neurons.

Two different approaches were used to increase the intracellular levels of E2F1 transcription factor; directly over-expressing E2F1 and over-expressing adenovirus oncogene E1A that forms a complex with Rb and p107 proteins leading to the release of active E2F1. (In proliferating cells, E1A becomes disassociated from E2F1.[9,16,22]) Also, in proliferating cells, E1A over-expression has been demonstrated to induce G1 to DNA synthesis phase transition.[8,23]

Post-mitotic granular neural cells were transfected with E2F1 or E1A cDNAs cloned into pRcCMVneo expression vector (Invitrogen) using the Transfectam (Promega) transfection protocol. After transfection, the neurons were grown for an additional one, two, or three days in the presence of BrdU and processed for immunostaining to detect BrdU incorporation, expression of neuronal markers, and E1A or E2F1 proteins.

Transfection of E1A and E2F1 expressing plasmids into cerebellar granular neurons stimulated, respectively, 37% and 43% of the successfully transfected neurons to become BrdU positive 24 hours after transfection (FIG. 1, Table 2). No DNA synthesis was detected in E1A- or E2F1-negative neurons. Time course analyses of BrdU incorporation reveal that DNA synthesis continues at least during the first three days after transfection.

In contrast, no DNA synthesis and expression of E1A or E2F1 was detected in untransfected neurons or in neurons transfected with helix-loop-helix transcription factors ME1 and ME2 (Neuman et al., Eur. J. Neurosci., 5:311–318 (1993)) cDNAs (Table 2) or pRcCMVneo vector without CDNA.

TABLE 2

Effect of expression of different cDNAs on BrdU incorporation in differentiated cerebellar neurons in vitro

| Transfection construct | Number of E1A or E2F1 positive neurons | Number of BrdU positive neurons | % E1A or E2F1 positive neurons that are BrdU positive |
| --- | --- | --- | --- |
| untransfected | 0 | 0 | 0 |
| pRcCMV | 0 | 0 | 0 |
| pRcE1A$_{13S}$ | 10.2 ± 6.9 | 3.7 ± 2.3 | 37 |
| pRcE2F1 | 8.5 ± 5.1 | 3.6 ± 1.5 | 43 |
| pRcME1 | 0 | 0 | 0 |
| pRcME2 | 0 | 0 | 0 |

Number represent means ±S.D. from 10 independent experiments. The number of immunostained neurons were counted in three areas (6 mm$^2$) of culture chamber.

EXAMPLE 3
Induction of DNA Synthesis In Cortical Neurons Of Adult Rats In Situ Using E2F1 And Adenovirus E1A cDNAs Neurons in the neocortex express a relatively high level of Rb protein (Okano et al., *Neurosci.*, 13:2930–2938 (1993)) which may inactivate transfected E2F1. To overcome this possibility, E2F1 and E1A expressing plasmids were mixed (1:1) and packed into immunoliposomes coated with antibodies against the cell surface protein Thy 1.1 to target the liposomes to neurons (Geisert and Holmberg, manuscript submitted (Attached as Appendix 1)). The present inventors hypothesized that E1A would bind to Rb resulting in the release of endogenous E2F1 that is expressed in the adult brain and protect transfected E2F1 from binding to Rb. (E2F is expressed in the adult brain (Helin et al., *Cell*, 70:337–350 (1992)).

Adult rats (over 6 weeks) were anesthetized using ketamine (85 mg/kg) and xylazine (13 mg/kg). Stereotaxic surgery was performed to inject 10 $\mu$l of immunoliposomes containing either 0.25 $\mu$g of pRcCMV vector, pRcCMV-$\beta$-gal ($\beta$-gal cDNA cloned into pRcCMVneo), or pRcCMV-E1A$_{13S}$/pRcCMV-E2F1 mixture (1:1) (a mixture of E1A$_{13S}$ cDNA cloned into pRcCMVneo and E2F1 cloned into pRcCMVneo) into the parietal cortex of adult rats. Injections were made 4 mm posterior to the bregma, 5–5.5 mm lateral to the midline, and 3.0–3.5 mm depth in the parietal cortex over a five minute period and the needle remained in place for an additional 10 minutes.

Nine or 33 hours after immunoliposome injection, BrdU solution (15 mg/ml in 0,9% NaCl, 0.007N NaOH; 50 mg g$^{-1}$ body weight) was injected intraperitoneally every 3 hours during a 24 hour period to identify DNA synthesizing cells. One half hour after the final injection, brains of anesthetized animals (see above) were fixed by transcardial perfusion with 4% paraformaldehyde. Triple immunostaining was performed on 8 $\mu$m cryostat sections as described above. As an additional step, sections were incubated with trypsin solution (10 mM Tris pH 7.8, 0.1% trypsin and 0.1% CaCl) for 10 minutes at room temperature after rehydration.

Immunoliposomes were prepared as described, e.g., in Holmberg et al., *Biochem. Biophys. Res. Comm.*, 165:1271–1278 (1989). The immunoliposomes were diluted to a concentration of 1 mg/ml total lipid. Plasmid DNA and Thy 1.1 antibody concentrations were 0.025 mg/ml and 0.25 mg/ml, respectively.

Figure 2A:
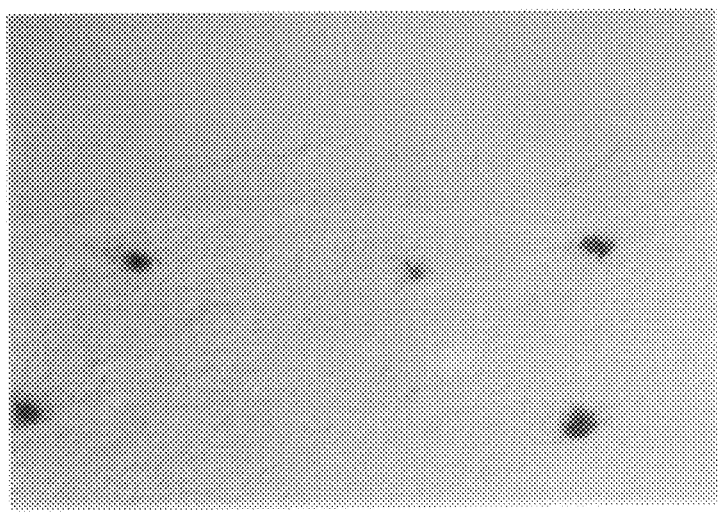
FIG. 2a. Cortical neurons were transfected with pRcCMVβ-gal CDNA and visualized for β-gal expression.

Immunoliposome mediated DNA transfer was used to introduce E1A and E2F1 into rat cortical neurons. Transfections using $\beta$-galactosidase cDNA demonstrated high efficiency of immunoliposome mediated transfection (FIG. 2*a*, Holmberg et al., submitted (attached as Appendix 2)).

Figure 2B:
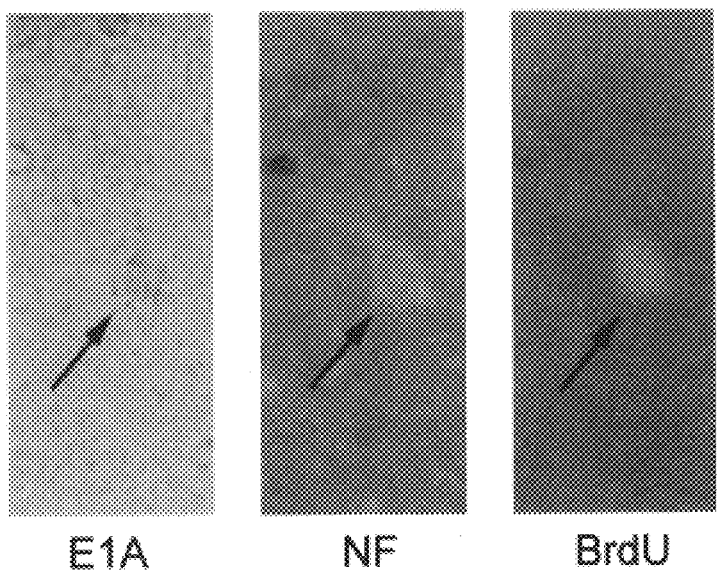
FIG. 2b and FIG. 2c. Cortical neurons in vivo were transfected with a mix of $E1A^{13S}$ and E2F1 cDNAs (1:1) using immunoliposomes and immunostained 33(b) and 57(c) hours post-transfection for E1A expression (left panel), NF-H expression (middle panel), and BrdU incorporation (right panel). Arrows indicate neurons that express E1A and are BrdU positive, arrowhead indicates E1A positive but BrdU negative neuron.
Figure 2C:
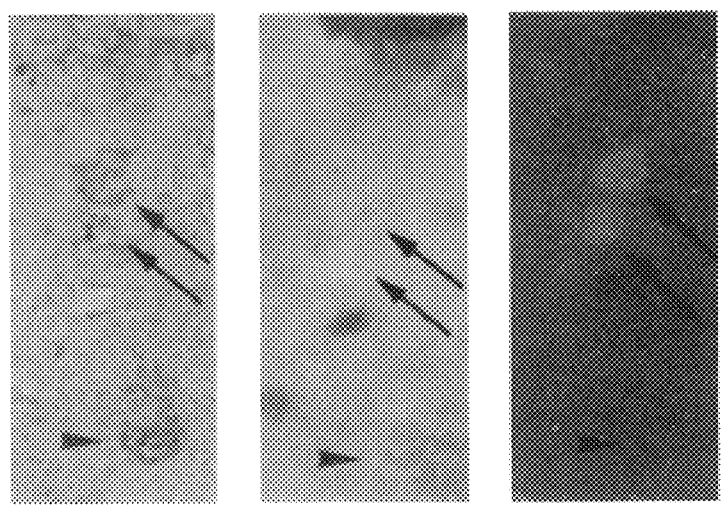

Expression of E1A and E2F1 results in DNA synthesis in cortical neurons (FIG. 2). Approximately fifteen and five percent of E1A expressing neurons become BrdU positive after 33 and 57 hours after transfection, respectively (Table 3). No DNA synthesizing neurons were detected in animals transfected with expression plasmids without CDNA.

TABLE 3

Effect of expression E1A and E2F1 on BrdU incorporation in adult rat cortical neurons in vivo

| Transfection construct | Number of E1A positive neurons/mm$^3$ | Number of BrdU positive neurons/mm$^3$ | % E1A positive neurons that are BrdU positive |
| --- | --- | --- | --- |
| control | 0 | 0 | 0 |
| pRcCMV | 0 | 0 | 0 |
| pRcE1A$_{13S}$ + pRcE2F1 33 h | 458 ± 192 | 66.7 ± 33.4 | 14.6 |

TABLE 3-continued

Effect of expression E1A and E2F1 on BrdU incorporation in adult rat cortical neurons in vivo

| Transfection construct | Number of E1A positive neurons/mm$^3$ | Number of BrdU positive neurons/mm$^3$ | % E1A positive neurons that are BrdU positive |
| --- | --- | --- | --- |
| pRcE1A$_{13S}$ + pRcE2F1 57 h | 788 ± 188 | 41.3 ± 33.7 | 5.2 |

Number represent means ±S.D. from 4 independent experiments. Triple labeled neurons were counted in 3 m2 areas surrounding the injection site in 10–12 serial sections (thickness 10 $\mu$m). Number of triple labeled cells was calculated based on these counts.

EXAMPLE 4

Integration of Introduced DNA Into Cortical Neurons After Stimulation Of DNA Synthesis To determine if the DNA delivered into postmitotic cortical neurons is stably integrated and functional, $\beta$-galactosidase cDNA ($\beta$-gal) under the control of CMV promoter was cotransfected with E2F1 and E1A cDNAs as described in Example 3.

Transfected brains were analyzed 3 days, 7 days, 3 weeks and 2 months after transfection for $\beta$-galactosidase expression using X-gal staining at pH higher than 7.5 (MacGregor et al., "Use of *E. coli* lacZ ($\beta$-galactosidase) as a reporter gene," *Gene Transfer and Transfection Protocols*, Ed. Murray, E. J., Human Press, Clifton, N.J., pp. 217–236 (1991)). This staining minimizes visualization of endogenous galactosidases and stains the transfected $\beta$-gal neurons blue. In control transfections, $\beta$-gal cDNA was transfected alone, without E1A and E2F cDNAs, in conditions where DNA synthesis is not induced.

After three and seven days, $\beta$-galactosidase activity was detectable in both control and experimental animals. Few $\beta$-galactosidase positive neurons were detectable after 3 weeks in control animals, but in the brains of experimental animals many blue neurons were detected. After 2 months, numbers of $\beta$-galactosidase positive neurons similar to those observed in the previous time points were detected in the brains of the experimental groups of animals, and no blue neurons were observed in the control animals. These data clearly demonstrate that by inducing DNA synthesis in neurons, one obtains long term intergration of DNA delivered into adult neurons.

TABLE 4

Integration of introduced DNA into adult cortical neurons in vivo.

| | number of $\beta$-galactosidase positive neurons/mm3 | |
| --- | --- | --- |
| Time | $\beta$-gal | $\beta$-gal + E1A and E2F1 |
| 3 days | 58 ± S | 61 ± 7 |
| 7 days | 43 ± 4 | 58 ± 4 |
| 3 weeks | 2 ± 1 | 42 ± 5 |
| 2 months | 0 | 43 ± 6 |

Numbers represent means ±S.D. from 4 independent experiments. $\beta$-galactosidase positive neurons were counted in 3 mm$^2$ areas surrounding the injection site in 10–12 serial sections (thickness 10 $\mu$m). Number of $\beta$-galactosidase positive neurons was calculated based on these counts.

The data demonstrate that stable integration and expression of delivered genes occurs in postmitotic neurons of the central nervous system (CNS). This occurs following the present invention in which DNA synthesis is induced in the target cell along with gene delivery. Accordingly, the present invention provides longer term production of protein in neurons, and demonstrates that the present invention may be used for gene-based therapies of the CNS. Further, this same method may be used to obtain stable integration of foreign DNA into any postmitotic cell of the body, since regulation of the cell cycle is not unique to neurons.

EXAMPLE 5

Integration Of Tyrosine Hydroxylase (TH) cDNA Into Postmitotic Human Neuronal Cells In Vitro Human neuronal cells NT2, which have many characteristics of adult differentiated neurons (Stratagene manual, NT2 cells), were used to demonstrate that stable integration of tyrosine hydroxylase (TH), a critical enzyme in dopamine synthesis, occurs after induction of DNA synthesis.

The NT2 cells were cultured in DMEM plus 10% fetal calf serum and differentiated neuronally for five weeks in the presence of 10 μM all-transretinoic acid (RA) (Stratagene manual). The cells were transfected by the Transfectam transfection procedure using 10 μg of pRcCMV, pRcCMV-TH (TH cDNA cloned into pRcCMVneo (TH cDNA sequence is in the Genebank and is shown in D'Mello et al., *J. Neurosci.*, 19:440–449 (1988) and the inventors obtained TH cDNA from B. B. Kaplan), pRcCMV-E1A$^{13S}$, or pRcCMV-E2F1 cDNAs. Five weeks differentiated cells were exposed to the DNA for 5 h in DMEM (Gibco) serum free media and then media was replaced with the growth media with RA. For TH immunostaining, fixed cells (4% paraformaldehyde plus 0.1% triton X-100) were incubated with TH mouse monoclonal antibody (Instar Corporation) overnight at 4° C. TH immunostaining was visualized using Vectastain ABC kit (Vector Laboratories) and 3,3'-diaminobenzidine tetrahydrochloride as a substrate for horseradish peroxidase. Cells were then examined using fluorescence microscopy with the appropriate filters.

NT2 cells differentiate neuronally and maintain a differentiated state in vitro after five weeks of RA treatment. No DNA synthesis was detected in differentiated NT2 cells based on 5-bromo-2'-deoxyuridine (BrdU) incorporation five weeks after RA treatment. The BrdU tests were performed as described above. To determine if the DNA delivered into neuronally differentiated NT2 cells is stably integrated and functional, TH cDNA under the control of CMV promoter was cotransfected with E2F1 and E1A cDNAs as discussed above. In control transfections, TH cDNA was transfected alone, without E1A and E2F cDNAs. Without transfection of E1A and E2F1, DNA synthesis is not induced in the controls.

Transfected cells were analyzed 3 days, 7 days, and 3 weeks after transfection for TH expression using antibodies against TH protein as discussed above. After three and seven days, TH immunoreactivity was detectable in both control and experimental cultures. Few TH positive cells were detectable after 3 weeks in control cultures, but in the experimental cultures hundreds of TH positive cells were detected. These data demonstrate that cotransfection of E2F and E1A DNA resulted in DNA synthesis and resulted in long term integration of TH DNA delivered into differentiated neurons.

TABLE 5

Integration of introduced tyrosine hydroxylase cDNA into neuronally differentiated NT2 cells.

| | number of TH positive cells in 60 mm culture dish Transfection | |
|---|---|---|
| Time | TH alone | TH + E1A and E2F1 |
| 3 days | 758 ± 21 | 761 ± 19 |
| 7 days | 643 ± 20 | 758 ± 31 |
| 3 weeks | 5 ± 1 | 723 ± 23 |

Numbers represent means ±S.D. from 4 independent experiments.

The data demonstrate that stable integration and expression of delivered genes occurs in postmitotic neurons. This occurs when DNA synthesis is induced in the target cell along with gene delivery. This forms the basis for application of this gene delivery method for gene-based therapies of the CNS.

EXAMPLE 6

Integration Of Tyrosine Hydroxylase (TH) cDNA Into Postmitotic Neurons Or Glia In Vivo In Treatment Of Parkinson's Disease Parkinsonism is a slowly progressive neurodegenerative disease of the central nervous system. Clinical symptoms are tremors at rest, rigidity, akinesia and postural impairment. A hallmark of the disease is reduction of the neurotransmitter dopamine in the basal ganglia which is caused by the loss of nerve cells in the brain stem. These dopamine producing neurons are located in the substantia nigra nucleus of the mesencephalon and project to and terminate in the basal ganglia. Major clinical signs and symptoms arise when around 80% of these neurons are lost.

The administration of the amino acid L-3,4-hydroxyphenylalanine (L-DOPA) is currently the most common treatment of the disease. L-DOPA is the immediate precursor of dopamine and after entering the neuron is converted to dopamine. Remission following this treatment indicates that the remaining dopamine neurons are adequately adaptive to restore basal ganglia activity. However, long term systemic L-DOPA treatments are complicated by side affects.

Amelioration of parkinsonian-like deficits in experimental animal models has also been accomplished by transplantation of fetal dopamine producing cells into the basal ganglia. With the potential ethical, legal, and histocompatibility issues associated with the use of fetal cells, investigators tested the feasibility of using DNA-secreting cells (chromaffin cells) dissected from the adrenal medulla. Animal experiments in rodents and non-human primates using cells from the adrenal medulla, however, have not been promising because of low survival and immunological rejection (Freed et al., *J. Neurosurg.*, 65:664–670 (1986); Hansen et al., *Exp. Neurol.*, 102:65–75 (1988)). The initial clinical trials with human Parkinson's disease patients also indicate a need for further basic research (Lindvall et al., *Ann. Neuro.*, 22:457–468 (1987; Goetz et al., *N. Engl. J. Med.*, 320:337–341 (1989)). The rate-limiting enzyme tyrosine hydroxylase (TH) is involved in the production of L-DOPA in neurons. The present inventors hypothesize that by increasing levels of TH at the neurons, one can also obtain L-DOPA at the neurons and thus treat Parkinson's disease.

This prophetic example is to stably insert a cDNA which codes for the TH protein into the remaining substantia nigra neurons and in neurons in close proximity to the substantia nigra neurons in the brain stem of patients with Parkinson's disease. The advantage of this gene therapy application is that the TH levels will be elevated in the remaining dopamine neurons of the substantia nigra and in neurons in close proximity to the substantia nigra neurons.

The L-DOPA drug treatments in Parkinson's disease patients have already demonstrated that the remaining dopamine neurons are capable of restoring basal ganglia activity. Instead of elevating the neurotransmitter levels in all the catecholamine/dopamine related pathways which occurs following systemic L-DOPA treatment, this application will elevate the TH levels only in the substantia nigra neurons and in neurons in close proximity to the substantia nigra neurons. The TH levels will be elevated in the specific dopamine producing neurons, which project to and terminate in basal ganglia. As discussed above, a hallmark of Parkinson's disease is reduction of the neurotransmitter dopamine in the basal ganglia.

Examples 4 and 5 above show that the present invention can be used to stably insert a functional cDNA encoding TH into postmitotic human neurons in vivo. In Example 5 above, the inventors showed the stable integration in vitro of TH cDNA into a human cell line that has many characteristics of differentiated human neuronal cells. This same or a similar cDNA construct should be functional in substantia nigra neurons and in neurons in close proximity to the substantia nigra neurons in the human brain to produce TH in vivo.

In Example 4, the invention was used to stably insert the beta-galactosidase gene into postmitotic cortical neurons in vivo in rats. Given the homology of regulation between species, one skilled in the art should be able to use a targeted liposome delivery system similar to the one in Example 4 to obtain stable integration of the TH DNA in the human brain.

Immunoliposomes specific for neurons are made similar to the immunoliposomes of Example 4 except that TH CDNA is substituted for beta-galactosidase cDNA. Moreover, one could design a liposome that is specific for a surface marker of substantia nigra neurons, and thus have a liposome that is even more specific for those particular neurons. Preferably, the liposomes will contain about 10–100 μg of the plasmid DNA (pRcCMV-TH, pRcCMV-E1A$^{13S}$, and pRcCMV-E2F1 in a 1:1:1 ratio).

Stereotaxic surgery similar to that performed in Example 4 will be performed to inject liposomes containing the inserted plasmids discussed above locally into the area of the substantia nigra neurons of a human or other animal. By selecting the specific area for the injection, one can limit transfection to the substantia nigra neurons and neurons in close proximity to the substantia nigra neurons.

Injecting small volumes of cells into brains of human patients is a rather non-invasive surgery (Lindvall et al. 1987), so injections of liposomes should not be invasive. One skilled in the art will be able to monitor the clinical signs of the patient over time to determine the effective dose and to determine whether subsequent administrations should be provided.

There are additions or alternatives to the above treatment. Given the fact that the parkinson-like symptoms can be ameliorated in experimental animal models by transplanting dopamine producing cells into cells within the basal ganglia, either glial cells or interneurons in the basal ganglia could be transfected with the similar cDNA constructs and liposome delivery system. One skilled in the art would be aware that the targeted liposomes would be constructed such that they recognize the particular cell type that is to be targeted.

EXAMPLE 7

Stable Integration Of Nerve Growth Factor (NGF) CDNA Into Postmitotic Basal Forebrain Cholinergic Neurons In Alzheimer's Patients Alzheimer's disease is a progressive neurodegenerative disease of the central nervous system resulting in senile dementia. Neuronal populations are differentially affected by the degenerative process with lesions throughout the brain. The entorhinal cortex and hippocampus are severely affected and forebrain cholinergic neurons and brain stem serotinergic and adrenergic neurons which project to the cortex and hippocampus are particularly vulnerable. There are a variety of cellular pathologies including the severally affected cytoskeleton (neurofibrillar tangle) and extracellular deposits of beta-amyloid protein (senile plaques).

It has been proposed that Alzheimers patients be treated with pluripotent neurotrophic factors (Terry, "Regeneration in Alzheimer Disease and Aging," *Advances in Neurology*, Vol. 59, pp. 1–4, Ed. F. J. Seil. Raven Press, Ltd., New York (1993)). There is a family of proteins called neurotrophic factors that have been shown to be responsible for growth and survival of neurons during development (Levi-Montalcine, *Science*, 237:1154–1162 (1987); Hofer et al., *Nature*, 331:261–261 (1988)) and to prevent death of neurons induced by lesions (Yan et al., *Nature*, 360:753–755 (1992; Koliatosos et al., *Neuron*, 10:359–367 (1993)). In the nervous system, the neurotrophic factors are synthesized and released from other neurons or support cells (glia). These factors bind to specific receptors on neurons, resulting in the activation of metabolic pathways which in turn are responsible for activating the production of proteins involved with growth and survival.

One of the characteristics of the Alzheimer brain is the reduction of cortical acetylcholine which can be caused by atrophy and depletion of nerve-growth-factor dependent (NGF) cholinergic forebrain neurons that project to the cerebral cortex and hippocampus. In animal models, lesion of this cholinergic pathway to the hippocampus results in cell loss in the forebrain cholinergic neurons which can be reversed by NGF (Tuszynski et al., *Ann. Neurol.*, 30:625–636 (1991)). Recombinant human nerve growth factor was infused into the lesion site of the adult primate brain.

In this prophetic example, cDNA encoding NGF protein will be stably inserted into the brain of Alzheimer patients. The source of NGF is Gene Bank Accession No. V01511. The CDNA would be stably inserted into the forebrain where damaged cholinergic neurons are localized. The cDNA constructs using the CMV promoter plasmids and the liposome delivery methods for delivery of the cDNA to the forebrain neurons would be similar to that described in Example 6 above. (NGF cDNA, of course, would be substituted for the TH cDNA.) Moreover, as discussed in Example 6, one skilled in the art would be able to monitor the patient to determine proper dosages and administration schedules.

There is an addition or alternative to this treatment of Alzheimers patients. Since the brain derived neurotrophic factor (BDNF) is at low levels in the hippocampus of Alzheimers patients (Phillips et al., *Neuron*, 7:695–702 (1990)), and since BDNF promotes survival of forebrain cholinergic neurons in vitro (Alderson et al., *Neuron*, 5:297–306 (1990)), cDNA constructs coding for BDNF protein could also be used to transfect hippocampal neurons in Alzheimers patients. The cDNA constructs using the CMV promoter plasmids and the liposome delivery methods for delivery of the cDNA to the hippocampal neurons would be similar to that described in Example 6 above.

EXAMPLE 8

Expression Screening System To Isolate cDNAs Which Induce Neurons To Proliferate Teratocarcinoma PCC7 cells (Pfeiffer et al., *J. Cell Biol.*, 88:57–66 (1981)) were used as a model system in these studies. PCC7 cells were grown in Dulbecco's modified Eagle medium (DMEM) containing 10% fetal calf serum (Sigma). Neuronal differentiation of PCC7 cells was induced with dibutyryl cyclic AMP (Bt$_2$cAMP, 1 mM) and all-trans retinoic acid (RA, 0.5 µm). PCC7 cells stop proliferation and differentiate into neuronal like cells after treatment Bt$_2$cAMP and retinoic acid RA. Differentiation is irreversible, as removal of Bt$_2$cAMP and RA does not cause differentiation.

To isolate genes whose expression causes differentiation and induction of proliferation, a subtraction cDNA library was made and cloned under the control of cytomegalovirus promoter. To generate the cDNA library, undifferentiated and neuronally differentiated teratocarcinoma PCC7 cells were used to isolate Poly A+ RNA using FastTrack mRNA isolation kit (Invitrogen). Twenty micrograms of Poly A+ RNA from undifferentiated cells was used to synthesize first strand cDNA. Oligo dT primer with a Not[1] restriction site at the 5' end (CTAGATCGCGAGCGGCCGCCCTTTTTTTTTTTTTTTTT),(SEQ ID NO:1) SuperScript RNaseH-reverse transcriptase (200 units per µg of Poly A+ RNA, Gibco), and $^{32}$P dCTP (50 µCi, >3000 Ci/mmol, Amersham) were used for first strand synthesis followed by alkaline treatment to remove RNA. First strand cDNA was hybridized to poly A+ RNA (200 µg) isolated from differentiated cells in sealed ampules (total volume 100 µl, buffer 0.5M sodium phosphate, pH 6.8, 300 mN NaCl, 2 mM EDTA and 0.2% SDS) for 18 h at 70° C. The hybridization mix was diluted to a final molarity of 0.08M sodium phosphate, loaded on a DNA grade hydroxylapatite column (4 ml volume, BioRad) and washed extensively with 0.08M sodium phosphate buffer (pH 6.8). Single stranded cDNAs were eluted in 10 ml of 0.15M sodium phosphate buffer. Column fractions (0.5 ml) exhibiting radioactivity above background were pooled, and the cDNAs were concentrated by butanol extraction followed by chromatography in STE buffer (100 M NaCl, 10 mM Tris-HCl pH 7.4, 1 mM EDTA) on a Sephadex G-25 column (Pharmacia). Single stranded cDNAs were mixed with 40 µg of poly A+ RNA from differentiated cells for the second cycle of hybridization and this yielded 0.6 µg of first strand cDNA (>95% efficiency). First strand cDNAs were hybridized with 5 µg of the original Poly A+ RNA isolate (undifferentiated cells) and the resulting DNA/RNA hybrids were precipitated for second strand synthesis with RNaseH and *E. coli* DNA polymerase 1 (Gibco). Blunt ends were created with T4 DNA polymerase, and the HindIII adapter

5' AGCTTGGCACGAG 3' (SEQ ID NO:2)

3' ACCGTGCTC 5' (SEQ ID NO:3)

was ligated to the cDNA. Preparation of cDNAs longer than 700 bp for ligation into the expression vector (pRc/CMV, Invitrogen) was performed by digestion with Not1 followed by size selection on a Sephacryl S 400 column (Pharmacia). cDNAs were cloned into the expression vector, pRcCMV (Invitrogen), between HindIII and NotI restriction sites. The library was divided into 26 aliquots and used to transform *E. coli* DH5 cells (MAX Efficiency, Gibco). Each aliquot yielded 5–8×10$^3$ colonies which were combined and grown for large-scale plasmid isolation (>plasmid< maxi kit, Qiagen). The cDNA expression library has 2×10$^5$ independent clones with an average insert size of 1.5 kb (range: 0.6–3.7 kb). The cDNA library in pRcCMV vector was transfected into neuronally differentiated PCC7 cells. PCC7 cells were differentiated in the presence of RA and Bt$_2$cAMP for 3 days before transfection. Transfection of the cDNA library was performed by the calcium phosphate coprecipitation technique using 20 µg of DNA per 100 mm tissue culture plates (Falcon) at a cell density of 2×10$^6$ cells per plate with an incubation time of 15–16 h. Each aliquot of the CDNA library (n=20) was used to transfect cells in 20 plates. Transfectants which were stably proliferating were identified following culture of cells in the presence of 400 µg/ml G418 (Gibco) for 18–21 days. Proliferating clones were isolated and subcloned.

Chromosomal DNA was isolated from these clones and used in PCR to amplify the transfected cDNAs. Genomic DNA was isolated using chromosomal DNA isolation kit (TurboGen, Invitrogen) and used as a template for amplification of cDNAs by polymerase chain reaction (PCR). Primers for cDNA amplification corresponding to flanking sequences in the pRcCMV vector (5' primer 5' AGCTCTCTGGCTAACTAGAGAAC (SEQ. ID. No: 6) and 3' primer 5' AGCGAGCTCTAGCATTTAGGTGA (SEQ.ID.No :7) were synthesized, and 35 cycles of PCR were performed using the following conditions: 92° C. 1.2 min., 58° C. 2 min., and 72° C. 4 min.

Amplified DNAs were cloned into EcoRV site of Bluescript plasmid (Stratagene) and sequenced from both ends using T3 and T7 primers. Isolated cDNAs with vector (pRcCMv) sequences were subcloned into pRcCMv expression vector between HindIII and NotI sites and retested on differentiated PCC7 cells. From the original three proliferating clones, 18, 21, and 17 cDNAs were retested. Three cDNAs from this second screening which induced proliferation were characterized. Sequence analyses (partial sequences) reveals that one cDNA is the mouse homolog of human E2F (Gene bank accession number M96577), and the other two cDNAs, which are Regulators of Neuronal Proliferation, coined RNP-1 and RNP-2 by the inventors here, have no significant homology to any GeneBank sequences.

EXAMPLE 9

Nucleotide Seauences Of RNP-1 and RNP-2

Determination of the sequences of RNP-1 and RNP-2 regulators of neuronal proliferation isolated from the expression cDNA library was accomplished as follows:

The HindIII-NotI fragments of both RNP-1 and RNP-2 were subcloned into Bluescript KS (Stratagene) plasmid and sequenced using Sequenase version 2 sequencing kit (purchased from United States Biochemicals). The partial nucleotide sequence of RNP-1 is as listed below:

```
                                                              (SEQ ID NO:4)
TTTTTCTTGT CTTTTGCTTC GGGCCGATTG TCGCTCACAA AAAAAGAAAA AAAACAAAAA      60

ACAAAAACCT GAGCTACCCT TTCCAAAACC CCGAGCAGCT CTCGTCGATT TCTGGAGCTC     120

GGAGCCGCCG GGTGCTGCGA GCGCCGGACG CAGGAGAGGG GAGCAAAGCA AATTGCGGCG     180
```

-continued

```
GGGGACCGAG CTCGCTCTGC TTGTCGCGGT CCTCTCCAGA AGCGCGCGAT GAAGGCGGTG    240

AGCCCGGTGC GCCCTCGGGC GTCAAGGCGC CGTCGGGCTG CGGCGGCGGG GAGCTGGCGG    300

TACGCTGCCT GGCGGAGCAC GGCCACAGCC TGGGTGGCTC GGCAGCCGCC GCCGCCGCTG    360

CGGCGGCCGC GCGGTGCAAG GCGGCCGAGG CGGCGGCCGA TGAGCCGGCG CTGTGCCTGC    420

AGTGCGATAT GAACGACTGC TACAGTCGCT GCGGAGGCTC GTGCCTACCA TCCCGCCCAA    480

CAAGAAAGTC AGCAAAGTGG AGATCCTGCA GCTGGCGCTG GAGACTCACC CTGCTTTGCT    540

GAGACAGCCG CCACCGCCCG CGCCACCTCT CCACCCGGCC GGGGCTTGTC CGGTCGCGCC    600

GCCGCGGACC CCACTCACCG CGCTCAACAC TGACCCGGCC GGCGCCGTGA ACAAGCAGGG    660

TGACAGCATT CTCTGCCGCT GAGCTGCGAT GGATGGCCAG GTGTGCGGCC GCCTGAGCAC    720

CAGCGAGCCA GGAGCCCTAG GAAGGGAGGG CCAGAGCAGA AATTAAGAGA AACAAGCCAC    780

CGGAGGAAAG GGGGGGAAAT CTTCAGCAAA TCTAGAGTCG TCTCGTCTTG TCATTCCAAG    840

AGAGAGAGAG AGAGAGAGAG AGAAGGGGAA AAATAAAACT TAAATTCACT TTTACTTTTT    900

TTGCACGTTC ACGAGCATTC ACCGTACGTA TTCTCTTCGT TCTTCTTTAT GACCGCTGTG    960

AATTGTACGT TTCTGTGGTT ATTTTTATCA CCCTTTTGAA GGTGCAGTTA AACTTCGAAG   1280

CTTAAGTGTT GTCGACCAGA CTGCTAAGTA GAAGAGCAAT CGTGAATCCA ACCTTAGAGG   1080

CTACATTGTG ACAAGGGAAC TGTTTTGTTT TTGAAGCTTT ACTAATATAC CAGAGCACTG   1140

TAGATATGTT GTTTTACATC TATTGTTTAA AATAGATGAT TATAACAGGG CGGGGAACTT   1200

TTTCTCTGCA AGAATGTTAC ATATTGTATA GATAAGTGAG TGACATTTCA TACCCTGTAT   1260

ATATAGAGAT GTTCTATAAG TGTGAGAAAG TATATGCGCT CTCGTGCCG              1309

(SEQ ID NO:5)
ATCATGGACT CAGTTCCGAA AACCAACAAA ATAGAACCGC GGTCCTATTC CATTATTCCT     60

AGCTGCGGTA TCCAGGCGGC TCGGGCTGCT TTGAACACTC TAATTTTTTA AAAGTAAACG    120

CTTCGGGCCC CGCGGGACAC TCAGCTAAGA GCATCGAGGG GGCGCCGAGA CGAAGGGGTC    180

TACAGAACTG CTGTCTTTTC AAAGTGAAAA TGCTCGCCCT TCATTTAACA CTAAAGCATA    240

ATGTCATGAA GTTTCATATC TGTACAGATT ATTTAAATCA TAGAAATGAA AAATGTTCTC    300

TGCTTGCTAC CAAAGGACAA ACTCTTGGAA ACGGACATTT TCTGCCCTCC TCGTGCCGAA    360

TTCATATCAA GCTTATCA
```

REFERENCES

The following documents, and the other references cited in this application are expressly incorporated by reference herein.

1. Kaplan, M. S. & Hinds, J. W. Science 197, 1092–1094 (1977).
2. Bayer, S. A. Exp. Brain Res. 46, 315–3323 (1982).
3. Altman, J. & Bayer, S. A. J.Comp. Neurol. 301, 365–381 (1990).
4. Angevine, J. B. & Sidman, R. L. Nature 192, 766–768 (1961).
5. Takahashi, T., Nowakowski, R. S. & Caviness, V.S.J. Neurocytol. 21, 185–197 (1992).
6. Nevins, J. R. Science 258, 424–429 (1992).
7. Mudryj, M., Devoto, S. H., Hiebert, S. W. et al. Cell 65, 1243–1253 (1991).
8. Schwarz, J. K. Devoto, S. H., Smith, E. J. et al. EMBO J. 12,1013–1020 (1993).
9. Chellappan, S. P., Hiebert, S., Mudryj, M. Cell 65, 1053–1061 (1991).
10. Hiebert, S. W., Chellappan S. P. Horowitz, J. M. Genes Dev. 6, 171–185 (1992).
11. Zamanian, M. & LaThangue, N. B. EMBO J. 11, 2603–2610 (1992).
12. Weintraub, S. J., Prater, C. A., Dean, D. C. Nature 358, 259–261 (1992). 13. Hamel, P. A., Gill, R. M., Phillips, R. A. et al. Molec. cell. Biol. 12, 3431–3438 (1992).
14. Dalton, S. EMBO J. 11, 1797–1804 (1992).
15. Shirodkar, S. Ewen, M., DeCaprio, J. A. et al. Cell 68, 157–166 (1992).
16. Zhu, L., Heuvel van den, S., Helin, K. et al. Genes Dev. 7, 1111–1125 (1993).
17. Okano, H. J., Pfaff, D. W., Gibbs, R. B. J. Neurosci. 13,2930–2938 (1993).
18. Bernards, R., Schacleford, G. M., Gerber, M. R. et al. Proc. Natn. Acad. Sci. U.S.A. 86, 6474–6478 (1989).

19. Helin, K., Lees, J. A., Vidal, M. Ct al. Cell 70, 337–350 (1992).
20. Gu, W., Scneider, J. W., Condorelli, G. et al. Cell 72, 309–324 (1993).
21. Holmberg, E. G., Maruyama, K., Litzinger, D. et al. Biochem. Biophys. Res. Comm. 165, 1271–1278 (1989).
22. Chellappan, S. P., Krause V. B., Kroger, B. et al. Proc. Natn. Acad. Sci. U.S.A. 89, 4549–4553 (1992).
23. Cao, L., Faha, B., Dembski, M. et al Nature 355, 176–179 (1992).
24. Neuman, T., Keen, A., Knapik, E. et al. Eur. J. Neurosci. 5, 311–318 (1993)
25. Goodrich, D. W., Wang, N. P., Qian, Y.-W. et al. Cell 67, 293–302 (1991).
26. Qin, X.-Q., Chittenden, T., Livingston, D. M. et al. Genes Dev 6, 953–964 (1992).
27. Johnson, D. G., Schwarz, J. K., Cress, D. W. et al. Nature 365, 349–352 (1993).
28. Lee, E. Y.-H.P. Chang, C.-Y., Hu, N et al. Nature 359, 288–294 (1992).
29. Jacks, T., Fazeii, A., Schmitt, E. M. et al. Nature 359, 295–300 (1992).
30. Clarke, A. R.,Maantag, E. R., et al. Nature 359, 251–254 (1992).
31. Suda et al., *NeuroReport*, 5:1749–1751 (1994).

APPENDIX 1

Transfecting Neurons and Glia in the Rat CNS Using pH-Sensitive Immunoliposomes Eldon E. Geisert, Jr., Nobel A. Del Mar*, Jesse L. Owens, Eric G. Holmberg*

*Department of Anatomy and Neurobiology, University of Tennessee, 855 Monroe Ave., Memphis, Tenn. 38163

**Department of Biology, University of Alaska Anchorage, Anchorage, Ak. 99508

*** Department of Chemistry/Physics, University of Alaska Anchorage, Anchorage, Ak. 99508

Summary

Immunoliposomes were constructed using antibody 5-113 (directed to an antigen on the external surface rat glial cells), the antibody Thy 1.1, and a non-immune antibody. The antibodies were conjugated to N-gluytaryl-phosphatidylethanolamine. The conjugated antibodies, β-galactosidase plasmid under the control of the Cytomegalovirus promoter, and other lipid components were constructed into liposomes. The three different types of immunoliposomes were injected into the brain and spinal cord of adult rats. In all animals, the X-gal reaction product was seen in neurons, astrocytes and vascular elements. There appeared to be an increase in neuronal labeling when animals were injected with Thy 1.1 conjugated liposomes and there was an increase in glial labeling in animals injected with 5-113 liposomes. In spinal cords, the immunoliposomes appear to penetrate a substantial distance, transfecting neurons several centimeters from the site of delivery. These data suggest that immunoliposomes may provide an effective transfection system for gene delivery in the CNS.

Keywords: Liposomes, β Galactosidase; Plasmid DNA; Neuronal transfection; Spinal cord; Gene therapy

Introduction

The study of gene expression and the use of genetic therapy in terminally differentiated cells of the nervous system requires the delivery of foreign genes and promoters into neurons. One approach is the use of gene transfer by a viral system. The Herpes simplex virus vector is one of the viral systems used for gene delivery in the CNS [1,3,4]. Another system uses the adenovirus to infect nerve cells with a high efficiency both in vitro and in vivo [9]. An alternative method is the use of lipid based carrier systems as a means of delivering plasmid DNA directly into the cells of the brain and spinal cord [8]. Several carrier systems use cationic lipid-phosphatidylethanolamine mixtures to form a lipid ligand complex [11]; however, there is a lack of specificity in these delivery systems and a potential problem of cellular toxicity.

A further refinement to this approach is the use of liposomal transfection systems that are constructed to increase the specificity of cellular targeting. Holmberg et al. [6] demonstrated an increase in targeting specificity of liposomes constructed of lipids covalently linked to monoclonal antibodies (immunoliposomes). These immunoliposomes deliver biologically active substances with an increase of targeting efficiency combined with a low cellular toxicity. In a previous study [7], we used a pH-sensitive immunoliposome composed of phosphatidylethanolamine, cholesterol and oleic acid to deliver plasmid DNA into cultured rat glial cells. In the present study, two monoclonal antibodies were used in an attempt to target the liposomal delivery system within the brain and spinal cord.

Liposomes were produced using a number of different components supplied by three different vendors: (1) Avanti Polar Lipids, Inc. (Alabaster, Ala.), Dioleyphosphatidylethanolamine (DOPE) and 18:1 N-glutarylphosphatidylethanolamine (NGPE); (2) Pierce (Rockford, Ill.), 1-ethyl-3(3-dimethylaminopropyl) carbodiimide (EDC) and hydroxysulfosuccinimide (S-NHS); and (3) Sigma Chemical Co. (St. Louis, Mo.), all other chemicals. Several different monoclonal antibodies were used in the-construction of the immunoliposomes. The Thy 1.1 monoclonal antibody was produced using a cell line (ATCC TIB 100) purchased from American Type Culture Collection. The monoclonal antibody 5-113 was produced in one of the author's laboratories (EEG). Monoclonal antibodies were purified from tissue culture supernatant. The monoclonal antibody 5-113 is an IgM antibody that recognizes an unknown epitope on the external surface of cultured astrocytes. The mAb 5-113 is described in recent paper [7]. Non-immune IgM was purchased from ICN (Irvine, Calif.).

Plasmids expressing the marker gene β-galactosidase were purchased from Promega Corp. (Madison, Wis.). The expression of the protein was under the control of either the SV40 early promoter (pSv-β-galactosidase) or the cytomegalovirus promoter (pCMVβ). The plasmid DNA was amplified in *E. coli* Dh5-alpha cells and recovered by alkaline extraction. The final purification of the plasmid was achieved using an isolation Qiagen Maxi Kit (Qiagen Inc., Chatsworth, Calif.).

Immunoliposomes containing the plasmid DNA were prepared in a manner similar to that previously described [6]. NGPE was dried in a stream of nitrogen and dissolved in a MES (2-(n-morpholino)ethanesulfonic acid hemisodium salt) buffered solution of octylglucoside (pH 5.5). The dissolved lipid was activated in the presence of EDC and S-NHS and incubated for 10 minutes. The solution was neutralized with NaOH, the antibody was introduced, and the solution was allowed to react at 4° C. for 10 hours. DOPE, cholesterol and oleic acid at a molar ratio of 4:4:2 were hydrated with NGPE conjugated antibody mixture and titrated with octylglucoside until all lipids dissolved. Plasmid DNA was added and the mixture was dialyzed for 48 hours at 40C. The liposomes were sized through a 0.4 um Nucleopore membrane and the liposomes were adjusted to a concentration of 1 mg of total lipid/ml of solution.

Two different experimental models were used to test the effectiveness of the immunoliposomes in delivering plasmid DNA within the CNS. In the first, the brain was injured by cutting through the cerebral cortex, the internal capsule and the fimbria with a scalpel blade and implanting a cannula for future delivery of the immunoliposomes. The general surgical procedures used in making the lesion and for implanting the cannula were previously described [5]. In brief, Sprague-Dawley rats (250 g) were anesthetized with sodium pentobarbital (60 mg/kg) and sterile surgery was performed. A single lesion was made unilaterally by passing a scalpel through the cerebrum in the coronal plane, an indwelling cannula (Plastics One) was implanted into the lateral ventricle on the side of the lesion, and the cannula was fixed to the skull with dental cement. Following a survival period of 60 days approximately, the animals were deeply anesthetized with sodium pentobarbital, the cannula was opened and the immunoliposomes were delivered at a rate of 0.5 µl/minute with a total volume of 10 µl. Two days after the delivery of the liposomes, the rats were overdosed with sodium-pentobarbital (100 mg/kg) and perfused through the heart with 4% paraformaldehyde in phosphate buffer (pH 7.4).

In the second set of experiments, a single injection of immunoliposomes was made into the spinal cord of Sprague-Dawley rats (250 g). The animals were deeply anesthetized, a laminectomy was performed at T8 and the dura was reflected. A 26 gauge needle was lowered 1 mm below the pial surface of the spinal cord and the immunoliposomes were delivered at a rate of 0.5 µl/min for a total volume of 5 µl, 10 µl or 15 µl. A small piece of gel foam was placed over the spinal cord, and the incision was sutured closed. The animals were monitored continuously until they recovered from the anesthesia. There were no noticeable problems associated with the surgery, the rats were able to bear weight on both hind legs and were capable of accessing their food and water. After a survival period of two days the animals were overdosed with sodium pentobarbital and perfused through the heart with fixative as described above. The brains and spinal cords were sectioned on a freezing microtome at 60 µm. The sections were rinsed in phosphate buffered saline (pH 7.2) and reacted with X-gal as described by Lim and Chae [10].

Four different types of liposomes were injected into the brain or the spinal cord: blank liposomes made of the identical lipid composition as the immunoliposomes with no conjugated antibody; liposomes conjugated to non-immune IgM; liposomes conjugated to the IgM 5-113; and liposomes conjugated to the IgM Thy 1.1. Liposomes that were not decorated with antibodies were injected through cannulas chronically implanted into two brains and into the spinal cords of two rats. When the tissues from these animals were examined there was a weak labeling at the site of injection, either at the end of the injection cannula or at the site of injection in the spinal cord. In all of the cases some of the glia surrounding the injection site were labeled and in the injections into the spinal cord a few neurons were positive for β-galactosidase enzyme. This type of labeling was not observed in sections from sham injected control animals. In these control cases, no blue reaction product was found anywhere in the brain or spinal cord. Thus, the presence of the blue X-gal is associated with the injection of the plasmid DNA.

Two different types of immunoliposomes (conjugated to 5-113 or to non-immune IgM) were tested in the adult rat brain. The liposomes were injected through a chronically implanted cannula into the region of the gliotic scar. Some of the labeling observed in the chronically injured brains was similar in all of the injections independent of the type of immunoliposomes delivered. The choroid plexus was labeled in all animals. In addition, at least some of the pericytes surrounding the vascular system within each of the brains were labeled. This pattern of labeling was independent of the type of antibody conjugated to the liposomes. The two brains that received injection of non-immune liposomes had the lightest labeling with modest diffuse labeling of ependymal cells, and some of the tissues adjacent to the ventricular system. The 5-113 immunoliposomes were injected into four brains. There was an intense labeling of the ependyma and gliotic scar near the tip of the injection cannula in all of these animals (Example 10D). Many of the cells within adjacent white matter were labeled and these cells had an astrocyte-like morphology. Two of the animals receiving the 5-113 immunoliposomes had a few lightly labeled neurons near the site of injection and in the superficial layers of the superior colliculus. In regions of white matter, such as the fimbria and corpus callosum, cells that were morphologically similar to astrocytes and oligodendrocytes were labeled with the X-gal reaction product.

The immunoliposomes were also tested in the spinal cords of normal rats. Three different immunoliposomes were injected: Thy 1.1 immunoliposomes into 6 animals; 5-113 immunoliposomes into 3 rats; and liposomes decorated with a non-immune IgM into 3 rats. In every case, cells within the CNS were transfected with the plasmid DNA, as indicated by the presence of the X-gal reaction product. As was observed in the brain, all of the animals that received plasmid DNA into the spinal cord demonstrated a labeling of the pericytes surrounding the blood vessels. Near the site of injection there was a labeling of some neurons and cells with an astrocyte-like morphology. This cellular labeling at the site of delivery was observed in all animals that received plasmid DNA, indicating that high concentrations of plasmid containing liposomes resulted in a generalized cellular transfection. Differences were observed when the different types of liposomes were delivered to the spinal cord.

In the animals injected with the non-immune liposomes, large cells with a neuronal morphology labeled near the site of the injection and many smaller cells were also labeled. Some of these smaller cells were associated with blood vessels and others were not. In cases where the X-gal reaction product extended out into the cellular processes of these smaller cells, the cells demonstrated an astrocyte-like morphology. In these animals there was labeling of cells associated with the blood vessels for the entire length of the spinal cords. There was a labeling of glial-like cells that faded within a centimeter of the injection site and neurons were only labeled within 2 to 3 mm of the injection site.

When immunoliposomes were decorated with the antibody 5-113 there appeared to be an increase in the number of cells that were transfected with the plasmid DNA. At the injection site in all animals there was a labeling of a few neurons, and a number of glial-like cells. Comparisons between the X-gal staining pattern in the 5-113 injected animals with the control animals revealed an increase in the number of cells labeled. The neuronal and glial labeling extended over a greater distance. The neuronal labeling was the heaviest immediately adjacent to the site of the injection and spread for approximately 1 cm in the rostral and caudal directions. Glial cells within the gray matter were also labeled for several centimeters of the spinal cord and in the white matter astrocyte-like cells were labeled up to 1 cm from the injection site.

The highest level of transfection was observed when the immunoliposomes were covalently linked to the Thy 1.1 mAb. Again in these animals, neurons and glia were labeled at the site of injection. In the white matter adjacent to the site of delivery, there was a labeling of glial-like cells and cells associated with the vascular supply (Example 10B). The most prominent feature in the Thy 1.1 immunoliposome injections was the large number of heavily labeled neurons within the gray matter of the spinal cord. Neurons of all sizes and in all locations were heavily labeled (Example 10C). To test the ability of small amounts of immunoliposomes to transfect neurons at a considerable distance from the injection sites, two rats received a small injection of 5 µl of Thy 1.1 immunoliposomes and the distance from the injection site was measured along the spinal cord. In both of these animals, neurons over the entire length of the spinal cord were transfected. The intensity of the X-gal reaction product was the highest within 5 mm of the injection site; however, neurons within the spinal cord were labeled from the sacral through the cervical levels of the cord.

The introduction and expression of genes in the CNS can be accomplished in several manners. Genes have been introduced into fibroblasts or brain cells prior to transplantation, using a viral vector [2]. This approach may be of use as a potential therapy for genetic or acquired neurological disorders. The expression of plasmid DNA would appear to eliminate potential problems associated with gene delivery by viral infections. However, Jiao et al. [8], have demonstrated that the expression of plasmid transfected genes is limited to only a few months, limiting the potential uses of this type of gene therapy to acute neurological disorders. For example, gene therapy following an acute injury or an acute treatment of the brain or spinal cord.

The present study demonstrates the delivery of gene construct into neurons using pH-sensitive immunoliposomes. These data indicate that pH-sensitive immunoliposomes are an effective means of delivering plasmid DNA to neurons and glial cells. Although there was a high level of transfection, the degree of specificity observed in the earlier tissue culture study [7], was not observed in this in vivo study. Potentially, the specificity of gene expression in this delivery system could be increased through the use of cell-specific promoters. The data from this study reveal the potential usefulness of the pH-sensitive immunoliposomes in gene therapy, for these liposomes are capable of delivering plasmid DNA over a considerable distance within the brain and spinal cord.

Example 10. The transfected cells taken from the normal spinal cord (10A, 10B and 10C) of an animal that received an injection of the Thy 1.1 immunoliposomes and from a rat that received a stab wound of the internal capsule ninety days before an injection of 5-113 immunoliposomes (Example 10D) were photomicrographed. At a low magnification of a tangential section of the spinal cord the neurons within the central gray matter were quite visible in Example 10A. These cells were viewed at a higher magnification in Example 10C. In addition to the cellular labeling within the gray matter, a number of cells were labeled with the X-gal reaction product in the white matter in Example 10B. Some of these cells appeared to be pericytes surrounding blood vessels and a few of the cells had an astrocyte-like morphology. In Example 10D the labeling at the glial scar was seen. The ependymal lining of the stab wound was heavily labeled with reaction product and within the surrounding tissue many small cells were labeled. Based on the size of these cells they appeared to be reactive astrocytes.

This work was supported by the Spinal Cord Society.

[1] Dobson, A. T., Margolis, T. P., Sedarati, F., Stevens, J. G. and Feldman, L. T., A latent, nonpathogenic HSV-1-derived vector stably expresses β-galactosidase in mouse neurons, Neuron, 5 (1990) 353–360.

[2] Fisher, L. J., Schinstine, M., Salvaterra, P., Dekker, A. J., Thai, L. and Gage, F. H., In vivo production and release of acetylcholine from primary fibroblasts genetically modified to express choline acetyltransferase, J. Neurochem. USA, 61 (1993) 1323–1332.

[3] Geller, A. I. and Breakefield X. O., A defective HSV-1 vector expresses *Escherichia coli* β-galactosidase in cultured peripheral neurons, Science, 241 (1988) 1667–1669.

[4] Geller, A. I. and Freese, A., Infection of cultured central nervous system neurons with a defective herpes simplex virus 1 vector results in stable expression of *Escherichia coli* β-galactosidase, Proc. Natl. Acad. Sci USA, 87 (1990) 1149–1153.

[5] Geisert, E. E. and Alley, C. D., Antiserum-induced growth of axon across lesions of the adult rat brain, Brain Res. Bull., 15 (1985) 19–28.

[6] Holmberg, E., Maruyama, K., Kennel, S., Klibanov, A., Torchilin, V., Ryan, U., and Huang, L., Target-specific binding of immunoliposomes in vivo. J. Lipsome Res. 1(4) (1990) 393–406.

[7] Holmberg, E. G., Quentin, R. R., Geisert, E. E. and Owens, J. L., Delivery of plasmid DNA to glial cells using pH-sensitive immunoliposomes, Biochem. Biophys. Res. Commun., 201 (1994) 888–893.

[8] Jiao, S., Acsadi, G., Jani, A., Felgher, P. L. and Wolff, J. A, Persistence of plasmid DNA and expression in rat brain cells in vivo, Exp. Neurol., 115 (1992) 400–413.

[9] Le Gal La Salle, G., Robert, J. J., Berrard, S., Ridoux, V., Stratford-Perricaudet, L. D., Perricaudet, M. and Mallet, J., An adenovirus vector for gene transfer into neurons and glia in the brain, Science, 259 (1993) 988–990.

[10] Lim, K. and Chae, C., A simple assay for DNA transfection by incubation of the cells in culture dishes with substrate for beta-galactosidase, BioTechniques, 7 (1989) 576–579.

[11] Stewart, M. J., Plautz, G. E., Del Buono L., Yang, Z., Xu, L., Gao, X., Huang, L., Nabel, E. G. and Nabel, G. J., Gene transfer in vivo with DNA-liposome complexes: safety and acute toxicity in mice, Hum. Gene Ther. USA, 3 (1992) 267–275.

APPENDIX 2

LIPOSOMAL DELIVERY OF PLASMID DNA TO GLIAL CELLS

Eric G. Holmberg*, Quentin R. Reuer*, Eldon E. Geisert*, and Jesse L. Owens*

Department of Chemistry/Physics and *Department of Biology University of Alaska Anchorage, Anchorage, Ak. 99508

*Department of Anatomy and Neurobiology, University of Tennessee, Memphis, Tenn. 38163

Summary

Immunoliposomes were constructed with an antibody specific to glial cells. They were used to examine the specificity and efficacy of cell type plasmid transfection.

Liposomes contained a β-galactosidase gene under control of an SV-40 promotor. Two different monoclonal antibodies of a difference subclass IgM and IgG, were examined for their targeting ability using immunoliposomes. Cultured C6 glioma (specific target cell type) and NIH 3T3 (control cell type, fibroblast) cells were transfected using these immunoliposomes. Results indicate a three-fold increase intransfection by the glial specific immunoliposomes, "gliasomes", in glial cell culture over control liposomes. Gliasomes were exposed to NIH 3T3 cells and showed no enhanced transfection over control liposomes. Gliasomes were tested for their specificity by the addition of excess antibody to the cell culture in order to saturate specific receptors on C6 glioma cells. Results indicate a reduced transfection, nearly three-fold, in cells that were saturated with excess antibody prior to exposure to the immunoliposomes.

Introduction

Lipid based carrier systems have been suggested as a possible solution to the problem of intracellular delivery of non-permeable molecules to cells. (1–4) Several lipid based carrier systems are commercially available for plasmid transfection of cell cultures. (5–6) The mechanisms of delivery and physical structures of these complexes are not well understood. Problems with these delivery systems include the specificity of delivery and their cellular toxicity.

The utilization of a liposome can possibly overcome the problems associated with lipid complex. Liposome based transfection systems have been refined by a variety of construction methods, component composition, and the chemical attachment of a variety of ligands such as proteins and carbohydrates. (7) Holmberg, et al., have shown a significant increase in the targeting efficiency of liposomes by the attachment of a monoclonal antibody to a liposome to form an immunoliposome. (8) Although the targeting efficiency of immunoliposomes has been shown to be increased and the apparent toxicity is low, the efficacy of delivery of biologically active agents has not been shown by this method.

We have utilized a pH-sensitive immunoliposome in conjunction with antibodies specific to glial cells to deliver plasmid DNA. Targeting antibodies were tested for specificity and cross reactivity by the addition of excess free antibody to the cells prior to transfection with glial specific immunoliposomes, gliasomes. Experimental Procedures Materials: Lipids were obtained from Avanti Polar Lipids, Inc. (Alabaster, Ala.). 1-Ethyl-3-(3-dimethylaminopropyl) carbodiimide (EDC) and N-hydroxysulfosuccinimide (S-NHS) were obtained from Pierce (Rockford, Ill.). Cholesterol, oleic acid, and all other chemicals were obtained from Sigma Chemical Co. (St. Louis, Mo.) Lipofectin and Transfectase were obtained from Gibco Laboratories. (Grand Island, N.Y.)

Antibodies: The monoclonal antibody 13–21 was generated from a fusion of lymph nodes in which two mice were immunized with a preparation of external membrane and associated proteins produced from mixed primary cultures of rat cerebral cortex. Cells from the neonatal rat cortex were cultured using methods previously described (9). Fragments of the external membrane of the cultured cells were prepared following the procedure described by Neff et al. (10) Antibodies were tested using an immunoblot analysis. Two subclasses of antibodies were determined, 5-113 was IgM subclass and 13–21 was IgG subclass, and both were used as targeting ligands. Both monoclonal antibodies were determined to be glia specific via indirect immunofluorescence staining. (Geisert, data not shown)

Immunoliposome Preparation: Immunoliposomes were prepared as described earlier (8) with the exception that plasmid DNA was added and the entire mixture was dialyzed for 48 hours at 4° C. in the final step. After dialysis, liposomes were sized four times through a 0.4 um Nucleopore membrane. Liposomes were separated from free plasmid DNA and unconjugated antibody on a BioGel Al.5M column. Liposomes were diluted to a concentration of 1mg/ml total lipid. Plasmid DNA and antibody concentrations were determined to be 0.025 mg/ml and 0.25 mg/ml, respectively, in the standard 1 mg/ml total lipid immunoliposome solution.

Plasmid Preparation: A DNA plasmid containing the marker gene β-galactosidase was obtained from Promega Corp. (Madison, Wis.). The plasmid DNA was amplified in *E. coli* DH5-alpha cells and recovered by alkaline extraction. (11) Plasmid was purified by passage through Quiagen columns. (Quiagen Inc., Chatsworth, Calif.)

Cell Culture Assay: NIH 3T3 fibroblasts and C6 glioma cells were seeded in six well plates and allowed to grow to 50%–75% confluency. Cells were rinsed with serum free media and allowed to equilibrate. Liposomes were added to the cells and gently rocked for 1 hour. Experiments designed to test the specificity of the liposomes transfection necessitated the addition of free antibody to the cell cultures prior to the addition of the immunoliposomes. After 1 hour of exposure to the free antibody, the cells were rinsed and immunoliposomes were added in serum free media with mild agitation. After rocking, the cells were rinsed and serum-containing media was added and cells were incubated at 37° C. in 5% $CO_2$ for 48 hours. Treated cells were rinsed and lightly fixed in 3% paraformaldehyde. Fixed cells were treated with X-gal as previously described. (12) Cells expressing β-galactosidase appear blue after the addition of X-gal. Cells were microscopically examined and counted with transformed cells expressed as a percent of the total cell population. Data were determined to be statistically significant using a students' t-test.

Results: Immunoliposomes were constructed using antibodies 5-113 and 13–21, which bind specifically to glial cells, and containing a β-galactosidase expressing gene. Bare liposomes, containing plasmid but with no attached targeting antibody, were constructed as a control for immunoliposomes. To compare the efficiency of immunoliposome transfection with other commercially available methods, cells were transfected using lipofectin and transfectase. Cells were also exposed to an aliquot of free plasmid.

Example 11 demonstrates the percent of transfected cells versus the transfection method for C6 glioma cells. Results in Example 11 indicate that maximal transfection occurred when cells were exposed to immunoliposomes with conjugated antibody 5-113 when identical concentrations (1μg lipid/well of cells, 75% confluent) of immunoliposomes were added to the cells. The transfection rate was 43.7±4.2% (n=3) as determined by differential cell counting. A smaller percentage of cells were transfected when exposed to 13–21 conjugated immunoliposomes, 18.1±1.5% (n=3) of the cells were transformed. Background transfection via liposomes is quantified by the addition of bare liposomes. The transfection efficiency for bare liposomes was 10.2±0.97% (n=3).

C6 Glioma cells were transfected via two commercially available methods and by the addition of free plasmid. Results indicate a transfection rate of 4.3±2.1% (n=3) with lipofectin. No detectable transfection was observed when cells were transfected with Transfectase or free plasmid. (Data not shown for Transfectase)

To examine the transfection specificity to cell type of 5-113 and 13–21 immunoliposomes, NIH 3T3 fibroblasts were exposed via the above mentioned transfection methods. Example 12 demonstrates the percentage of cells transfected versus the transfection method. Maximal transfection occurred when lipofectin was used as a transfection carrier, 17.4±2.6% (n=3) transfection efficiency was observed. Results with bare liposomes indicate a transfection frequency of 10.1±1.5% (n=3), a rate nearly identical to that of the C6 glioma cells. No detectable transfection was observed when cells were exposed to tranfectase (data not shown), free plasmid, or 5-113 immunoliposomes. A very low transfection rate, 3.1±1.7% (n=3) was observed when 3T3 cells were exposed to 13–21 immunoliposomes.

To test the specificity of transfection, via immunoliposomes, cells were presaturated with free antibody prior to exposure to the immunoliposomes. Presaturation of the cell-surface antigens should block specific sites and reduce the specific binding to approximately background levels. Example 13 demonstrates the percent of transformed C6 glioma cells versus transfection vehicle when cells were presaturated by either specific antibody or with the addition of no antibody. Little variation in background transfection levels was observed for the addition of plasmid containing bare liposomes with or without the prior addition of free antibody.

Antibody 5-113 immunoliposomes were added to C6 glioma cells in culture with and without the presaturation by either antibody. A transfection level of 42.8±4.2% (n=3) was observed with the addition of 5-113 immunoliposomes. Transfection levels were reduced three fold with the prior addition of 5-113 free antibody (13.2±2.2%, n=3) to the cells. Transfection levels were reduced approximately two-fold with the prior addition of antibody 13–21 (22.1±3.9%, n=3) when 5-113 immunoliposomes were added to the cells. 13–21 immunoliposomes were added to CG glioma with and without prior treatment of antibodies 13–21 and 5-113. Prior saturation of the cells with antibody 5113 resulted in a slight, but insignificant (P<0.50), increase in transfection to 34.7±5.91% (n=3). Presaturation of the cells with antibody 13–21 prior to addition of 13–21 immunoliposomes resulted in an approximate 40% decrease in transfection efficiency to 17.7±2.7% (n=3).

Discussion: Holmberg et al. established successful targeting efficiency via the NGPE conjugated antibody/dialysis method of immunoliposome assembly. (8) A question exists regarding. immunoliposome efficacy with respect to their ability to deliver bioactive materials such as drugs or genes. In addition to successful delivery and expression of plasmid DNA we have tested two immunoliposome constructs with different subclasses of antibody directed to glial cells for a targeting ligand.

Results from Example 11 demonstrate a three fold increase in the percent of transfected cells with the use of the 5-113 antibody (IgM subclass) conjugated immunoliposomes over control liposomes and an approximately two fold increase in transfection efficiency with 13–21 antibody (IgG subclass) conjugated immunoliposomes over control liposomes. A consistent background level of transfection, approximately 10%, in both NIH 3T3 cells and C6 glioma cells was observed for transfection by control bare liposomes containing the plasmid. Specific immunoliposomes, "gliasomes", were more efficient in their transfection efficiency than the cationic lipid complex methods using lipofectin and transfectase.

The cell specificity of transfection is illustrated by the increased transfection of C6 glioma cells when compared to identical transfections with NIH 3T3 cells. A increase in transfection frequency occurred with both types of gliasomes. 5-113 immunoliposomes demonstrated no measurable ability to transfect NIH 3T3 cells in culture whereas a —44% transfection efficiency was observed with C6 glioma. Some NIH 3T3 cells were transfected with 13–21 immunoliposomes but with an efficiency of approximately 10 fold less than the transfection efficiency of C6 glioma.

Specificity was also demonstrated by the reduction in transfection of C6 glioma cells following presaturation with free antibody prior to transfection via immunoliposomes. Data from Example 13 indicate a three fold reduction in transfection rate from 5-113 immunoliposomes with presaturation of the cells with free 5-113. The addition of 13–21 prior to the addition of 5-113 immunoliposomes resulted in a reduced transfection efficiency. This effect could possibly be from a shared epitope or a steric hindrance of binding on the cells surface at or near the binding site. Transfection efficiency was reduced to background levels with the addition of free 5-113 prior to transfection with 5-113 immunoliposomes indicating a large amount of the binding is specific. Presaturation of the cells with either 5-113 or 13–21 had no significant effect on the transfection efficiency of bare liposomes. Examination of antibody 5-113 presaturated C6 cells prior to transfection with 13–21 immunoliposomes showed no significant increase in the transfection rate. This observation indicates that a shared epitope-is unlikely for the two antibodies and that a steric effect is probably the cause for decreased transfection for the 5-113 immunoliposomes with presaturation of 13–21. This effect could be due, in part, to the size of 5-113, IgM subclass, versus the size of 13–21, IgG subclass. A smaller reduction in transfection frequency was observed for 13–21 immunoliposomes with presaturation of 13–21, an approximate 30% reduction in transfection rate was observed.

In conclusion we have shown this mild conjugation technique and liposome assembly method can be used to construct immunoliposomes which greatly enhance transfection efficiency and specificity. This transfection method is more specific and efficient than lipid complex methods and bare plasmid containing liposomes. In addition the toxicity of this method is less than that of the retroviral methods. These liposomes have the potential to carry drugs or genes to target sites in vitro or in vivo for the treatment of disease. We have presently begun experiments to determine the feasibility of plasmid gene delivery in brain and spinal cord with glial specific immunoliposomes.

Acknowledament

This work was supported by a contract from the Spinal Cord Society, Fergus Falls, Minn.

References

1. Litzinger, D. C., and Huang, L. (1992) *Biochim. Biophys. Acta* 1113, 201–227.
2. Hug, P., and Sleight, R. G. (1991) *Biochim. Biophys. Acta* 1097, 1–17.
3. Collins, D., and Huang, L. (1987) *Cancer Res.* 47, 735–739.
4. Wang, C. Y. and Huang, L. (1987) *Proc. Nat. Acad. Sci. USA* 84, 7851–7855.
5. Felgner, P. L., Gadek, T. R., Holm, M., Roman, R., Chan, H. W., Wenz, M., Northrop, J. P., Ringold, G. M., and Danielsen, M., (1987) *Proc. Nat. Acad. Sci. USA* 84, 7413–7417.
6. Chang, A. E. Y., and Brenner, D. G., (1988) *Focus* 65–69.

7. Wright, S., and Huang, L., (1989) *Adv. Drug Delivery Rev.*, 3, 343–389.
8. Holmberg, E, Maruyama, K., Litzinger, D., Wright, S., Davis, M., Kabalka, G., Kennel, S., and Huang, L., (1989) *Biochem. Biophys. Res. Comm.* 165, 1272–1278.
9. Geisert, E. E., Jr., and Stewart, A. M., (1991) *Deve. Biol.* 143, 335–345.
10. Neff, N. T., Lowery, C., Decker, C., Tovar, A., Damsky, C., Buck, and Horwitz, A. F., (1982) *J. Cell. Biol.* 95, 654–666.
11. Birnboim, H. C., and Doly, J. (1979) *Nuc. Acids Res.* 7, 1513–1523.
12. Lim, K., and Chae, C. B., (1989) *Biotechniques* 7, 576–579.

Example 11

15 µl of liposomes (1 mg/ml total lipid, 0.25 mg/ml antibody, 0.025mg/ml plasmid DNA) were added to C6 glioma cells at 75% confluence. After exposure to immunoliposomes cells were fixed and assayed for expression of β-galactosidase. Transformed cells were counted and were expressed as a function of the percent total cell population ±S.D. (n=3). Bare liposomes had approximately 10% transfection. 5-113 immunoliposomes had approximately 44% transfection. 13–21 immunoliposomes had approximately 19% transfection. Lipofectin had approximately 5% transfection. Free plasmid transfection had less than 1% transfection.

Example 12

15 µl of liposomes (1 mg/ml total lipid, 0.25mg/ml antibody, 0.025 mg/ml plasmid DNA) were added to NIH 3T3 cells at 75% confluence. After exposure to immunoliposomes cells were fixed and assayed for expression of β-galactosidase. Transformed cells were counted and were expressed as a function of t he percent total cell population ±S.D. (n=3). Bare liposomes had approximately 10% transfection. 13–21 immunoliposomes had approximately 3% transfection Lipofectin had approximately 18% transfection. 5-113 immunoliposomes and free plasmid transfection had less than 1% transfection.

Example 13

C6 glioma cells were presaturated with antibodies 5-113, 13–21, and control buffer at 4° C. prior to exposure to bare liposomes, 5–133 immunoliposomes, and 13–21 immunoliposomes at 37° C. to block specific binding sites located on the cell surface prior to transfectiokn. Transformed cells were counted and were expressed as a function of the percent total cell population ±S.D. (n=3). Control buffer blocked with bare liposomes had approximately 10% transfection; control buffer blocked with 5-133 immunoliposomes had approximately 43% transfection; and control buffer blocked with 13–21 immunoliposomes had approximately 34% transfection. Antibody 5-113 blocked with bare liposomes had approximately 14% transfection; antibody 5-113 blocked with 5-133 immunoliposomes had approximately 13% transfection; and antibody 5-113 blocked with 13–21 immunoliposomes had approximately 36% transfection. Antibody 13–21 blocked with bare liposomes had approximately 10% transfection; antibody 13–21 blocked with 5-133 immunoliposomes had approximately 22% transfection; and antibody 13–21 blocked with 13–21 immunoliposomes had approximately 18% transfection.

We claim:

1. A method for inducing nucleic acid synthesis in a differentiated neuron in vivo comprising:
obtaining at least one vector comprising nucleic acid encoding a desired protein and an E2F regulator or an E1A regulator, or both an E2F regulator and an E1A regulator;
wherein the vector is injected into or near the peripheral nervous system and is not injected into the brain or the central nervous system of an animal.

2. A method as in claim 1, wherein the vector(s) are associated with immunoliposomes.

3. A method as in claim 1 wherein the vector(s) comprise pRcCMV.

4. A method as in claim 3, wherein the vector(s) comprise the E2F regulator.

5. A method as in claim 3, wherein the vector(s) the E2F1 regulator.

6. A method as in claim 3, wherein the vector(s) comprise the E1A regulator.

7. A method for integrating DNA encoding a desired protein in a differentiated neuron in vivo comprising:
obtaining a vector comprising nucleic acid encoding an E2F regulator, an E1A regulator, or both an E2F regulator and an E1A regulator, wherein the vector can be used to express the DNA encoding a desired protein in a neuron;
obtaining DNA encoding a desired protein; and
cotransfecting a differentiated neuron with the vector and the DNA encoding the desired protein such that the DNA encoding the desired protein is integrated in the differentiated neuron and the desired protein is produced;
wherein the vector is injected into or near the peripheral nervous system and is not injected into the brain or the central nervous system of an animal.

8. A method as in claim 7, wherein the vector is included in immunoliposomes.

9. A method as in claim 7, wherein the desired protein is a neurotrophic factor.

10. A method as in claim 7, wherein the vector comprises pRcCMV and nucleic acid encoding an E2F regulator, an E1A regulator, or both an E2F regulator and an E1A regulator.

11. A method as in claim 7, wherein the vector comprises pRcCMV and nucleic acid encoding E2F regulator.

12. A method as in claim 7, wherein the vector comprises pRcCMV and nucleic acid encoding E2F1 regulator.

13. A method as in claim 7, wherein the vector comprises pRcCMV and nucleic acid encoding E1A regulator.

14. A method as in claim 7, wherein the desired protein is tyrosine hydroxylase.

15. A method as in claim 14, wherein the neuron produces catecholamine.

16. An improved method of inducing neurons to express DNA encoding a desired protein of the type wherein the DNA encoding the desired protein is introduced into the neuron, the improvement comprising:
cotransfecting the DNA encoding the desired protein with nucleic acids encoding at least one of the members of the group consisting of E2F and E1A.

17. The method of claim 16 wherein the E2F is chosen from the group consisting of E2F1, E2F2, and E2F3.

18. The method of claim 16 wherein the E2F is chosen from the group consisting of E2F1, E2F2, and E2F3.

19. An improved method of inducing neurons to express DNA encoding a desired protein of the type wherein the DNA encoding the desired protein is introduced into the neuron, the improvement comprising:
introducing DNA encoding the desired protein in combination with factors that bind to Rb.

20. The method of claim 19 wherein the factor that binds to Rb is an antibody.

21. The method of claim 19 wherein the factor that binds to Rb is E2F.

22. A method for integrating DNA encoding a desired protein into a differentiated neuron, the method comprising co-transfecting a differentiated neuron with DNA encoding a desired protein and DNA encoding either (a) an E2F regulator, (b) an E1A regulator, or (c) both an E2F regulator and an E1A regulator wherein the co-transfection step is performed in vitro.

23. The method of claim 22 comprising a step of transplanting the co-transfected neuron(s) into an animal, wherein the animal is either human or non-human.

24. A method for integrating DNA encoding a desired protein into a differentiated neuron, the method comprising co-transfecting a differentiated neuron with DNA encoding a desired protein and DNA encoding either (a) an E2F regulator, (b) an E1A regulator, or (c) both an E2F regulator and an E1A regulator wherein the co-transfection step is performed in vivo in an animal, the animal being either human or non-human.

25. The method of claim 24 wherein the DNA is introduced by injection into the brain or central nervous system of the animal.

26. The method of claim 24 wherein the DNA is introduced by injection into or near the peripheral nervous system of the animal.

* * * * *

SEQUENCE LISTING

```
<160> NUMBER OF SEQ ID NOS:  7

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence:oligo dT
      primer with Not1 restriction site

<400> SEQUENCE: 1
ctagatcgcg agcggccgcc cttttttttt tttttttt                            38

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence:HindIII
      adapter

<400> SEQUENCE: 2
agcttggcac gag                                                       13

<210> SEQ ID NO 3
<211> LENGTH: 9
<212> TYPE: DNA
<213> ORGANISM: Artificial Sequence
<220> FEATURE:
<223> OTHER INFORMATION: Description of Artificial Sequence:HindIII
``` adapter

<400> SEQUENCE: 3 accgtgctc                                                          9

<210> SEQ ID NO 4
<211> LENGTH: 1309
<212> TYPE: DNA
<213> ORGANISM: Mus sp.

<400> SEQUENCE: 4
tttttcttgt cttttgcttc gggccgattg tcgctcacaa aaaagaaaa aaaacaaaaa    60 acaaaaacct gagctaccct ttccaaaacc ccgagcagct ctcgtcgatt tctggagctc   120
ggagccgccg ggtgctgcga gcgccggacg caggagaggg gagcaaagca aattgcggcg   180
ggggaccgag ctcgctctgc ttgtcgcggt cctctccaga agcgcgcgat gaaggcggtg   240
agcccggtgc gccctcgggc gtcaaggcgc cgtcgggctg cggcggcggg gagctggcgg   300
tacgctgcct ggcggagcac ggccacagcc tgggtggctc ggcagccgcc gccgccgctg   360
cggcggccgc gcggtgcaag gcggccgagg cggcggccga tgagccggcg ctgtgcctgc   420
agtgcgatat gaacgactgc tacagtcgct gcggaggctc gtgcctacca tcccgcccaa   480
caagaaagtc agcaaagtgg agatcctgca gctggcgctg gagactcacc ctgctttgct   540
gagacagccg ccaccgcccg cgccacctct ccacccggcc ggggcttgtc cggtcgcgcc   600
gccgcggacc ccactcaccg cgctcaacac tgacccggcc ggcgccgtga caagcaggg    660 tgacagcatt ctctgccgct gagctgcgat ggatggccag gtgtgcggcc gcctgagcac   720
cagcgagcca ggagccctag gaagggaggg ccagagcaga aattaagaga aacaagccac   780
cggaggaaag gggggggaaat cttcagcaaa tctagagtcg tctcgtcttg tcattccaag   840
agagagagag agagagagag agaaggggaa aaataaaact taaattcact tttacttttt   900
ttgcacgttc acgagcattc accgtacgta ttctcttcgt tcttctttat gaccgctgtg   960
aattgtacgt ttctgtggtt attttttatca ccctttttgaa ggtgcagtta aacttcgaag  1020
cttaagtgtt gtcgaccaga ctgctaagta gaagagcaat cgtgaatcca accttagagg  1080
ctacattgtg acaagggaac tgttttgttt ttgaagcttt actaatatac cagagcactg  1140
tagatatgtt gttttacatc tattgtttaa aatagatgat tataacaggg cggggaactt  1200
tttctctgca agaatgttac atattgtata gataagtgag tgacatttca tacctgtat  1260 atatagagat gttctataag tgtgagaaag tatatgcgct ctcgtgccg             1309

<210> SEQ ID NO 5
<211> LENGTH: 378
<212> TYPE: DNA
<213> ORGANISM: Mus sp.

<400> SEQUENCE: 5
atcatggact cagttccgaa aaccaacaaa atagaaccgc ggtcctattc cattattcct    60
agctgcggta tccaggcggc tcgggctgct ttgaacactc taatttttta aaagtaaacg   120
cttcgggccc cgcgggacac tcagctaaga gcatcgaggg ggcgccgaga cgaagggggtc  180 tacagaactg ctgtctttc aaagtgaaaa tgctcgccct tcatttaaca ctaaagcata   240
atgtcatgaa gtttcatatc tgtacagatt atttaaatca tagaaatgaa aaatgttctc   300
tgcttgctac caaaggacaa actcttggaa acggacattt tctgccctcc tcgtgccgaa   360
ttcatatcaa gcttatca                                                378

```
<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:primers
      corresponding to flanking sequences in vector
      pRcCMV

<400> SEQUENCE: 6
agctctctgg ctaactagag aac                                            23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:primers
      corresponding to flanking sequences in vector
      pRcCMV

<400> SEQUENCE: 7
agcgagctct agcatttagg tga                                            23
```